United States Patent
De Becdelievre et al.

(10) Patent No.: US 11,806,454 B2
(45) Date of Patent: Nov. 7, 2023

(54) WEARABLE BREAST PUMP SYSTEM

(71) Applicant: Chiaro Technology Limited, London (GB)

(72) Inventors: Thibault De Becdelievre, London (GB); Oliver Blanchard, London (GB); Georgia Thomas, Bristol (GB); Daniel John Thompson, Bristol (GB); Adam Rollo, London (GB); Paul Reid, Bristol (GB); Jonathan O'Toole, Bristol (GB); Jack Biltcliffe, London (GB); Clare Larkspur, Bristol (GB); Claudia Bruen, London (GB)

(73) Assignee: Chiaro Technology Limited, London (GB)

( * ) Notice: Subject to any disclaimer, the term of this patent is extended or adjusted under 35 U.S.C. 154(b) by 0 days.

(21) Appl. No.: 18/148,864

(22) Filed: Dec. 30, 2022

(65) Prior Publication Data

US 2023/0158215 A1     May 25, 2023

Related U.S. Application Data

(63) Continuation of application No. 17/907,347, filed as application No. PCT/GB2021/050764 on Mar. 26, 2021.

(30) Foreign Application Priority Data

Mar. 26, 2020 (GB) ...................................... 2004395

(51) Int. Cl.
   *A61M 1/06*      (2006.01)
   *A61M 1/00*      (2006.01)
   *A61M 39/22*     (2006.01)

(52) U.S. Cl.
   CPC .............. *A61M 1/067* (2021.05); *A61M 1/60* (2021.05); *A61M 39/22* (2013.01); *A61M 2205/42* (2013.01); *A61M 2209/088* (2013.01)

(58) Field of Classification Search
   CPC ............................................ A61M 1/06–0697
   See application file for complete search history.

(56) References Cited

U.S. PATENT DOCUMENTS 2,849,881 A     9/1958   Anderson
4,390,024 A     6/1983   Williams
(Continued)

FOREIGN PATENT DOCUMENTS

CN     101549180 A     10/2009
CN     105288759 A     2/2016
(Continued)

OTHER PUBLICATIONS

4MD Medical, "Assembling Spctra Breast Pump Parts," YouTube [online], dated Nov. 13, 2016, URL: http://www.youtube.com/watch?v=ChV8xQfcBxU.

(Continued)

*Primary Examiner* — Courtney B Fredrickson
(74) *Attorney, Agent, or Firm* — Sterne, Kessler, Goldstein & Fox P.L.L.C.

(57) ABSTRACT

A breast pump system comprises at least one wearable milk collection hub connected via an air line to a combined external air pump and control unit. Each milk collection hub comprises: (a) a breast shield made up of a breast flange and a nipple tunnel; (b) a flexible diaphragm that is configured to prevent milk from reaching the external air pump; (c) an outer shell that is configured to removably attach to the breast shield, such that, when attached, the breast shield and outer shell form a vessel for collecting milk; and (d) a diaphragm cap that is configured to be secured over the (Continued)

diaphragm, forms part of the front face of the outer shell, and includes a port connected to the air line.

33 Claims, 34 Drawing Sheets

(56) References Cited

U.S. PATENT DOCUMENTS

| | | |
|---|---|---|
| 4,535,627 A | 8/1985 | Prost et al. |
| 4,673,388 A | 6/1987 | Schlensog et al. |
| 5,406,063 A | 4/1995 | Jelen |
| 5,474,683 A | 12/1995 | Bryant et al. |
| 5,542,921 A | 8/1996 | Meyers et al. |
| 5,941,847 A | 8/1999 | Huber et al. |
| 5,973,770 A | 10/1999 | Carter et al. |
| 6,045,529 A | 4/2000 | Nuesch |
| 6,090,065 A | 7/2000 | Giles |
| 6,227,936 B1 | 5/2001 | Mendoza |
| 6,328,709 B1 | 12/2001 | Hung et al. |
| 6,358,226 B1 | 3/2002 | Ryan |
| 6,383,163 B1 | 5/2002 | Kelly et al. |
| 6,440,100 B1 | 8/2002 | Prentiss et al. |
| 6,461,324 B1 | 10/2002 | Schlensog |
| 6,547,756 B1 | 4/2003 | Greter et al. |
| 6,579,258 B1 | 6/2003 | Atkin et al. |
| 6,663,587 B2 | 12/2003 | Silver et al. |
| 6,749,582 B2 | 6/2004 | Britto et al. |
| 7,048,519 B2 | 5/2006 | Fong et al. |
| 7,201,735 B2 | 4/2007 | Atkin et al. |
| D548,831 S | 8/2007 | Charlez |
| 7,312,554 B2 | 12/2007 | Vogeley |
| 7,314,400 B2 | 1/2008 | Fildan et al. |
| 7,641,629 B2 | 1/2010 | Yuen |
| 7,662,018 B1 | 2/2010 | Thompson et al. |
| 7,666,162 B2 | 2/2010 | Renz et al. |
| 7,776,008 B2 | 8/2010 | Renz et al. |
| 7,833,190 B1 | 11/2010 | Hall |
| 8,057,425 B1 | 11/2011 | Myers et al. |
| 8,118,772 B2 | 2/2012 | Dao et al. |
| 8,187,227 B2 | 5/2012 | Luzbetak et al. |
| 8,262,606 B2 | 9/2012 | Greter et al. |
| 8,282,596 B2 | 10/2012 | Greter et al. |
| 8,376,986 B2 | 2/2013 | Van et al. |
| 8,608,685 B2 | 12/2013 | Tashiro et al. |
| 8,702,646 B2 | 4/2014 | Garbez et al. |
| 8,801,495 B1 | 8/2014 | Guindon |
| 8,876,760 B2 | 11/2014 | Bosman et al. |
| 8,926,556 B2 | 1/2015 | Van et al. |
| 9,033,913 B2 | 5/2015 | Khalil et al. |
| 9,173,587 B2 | 11/2015 | Van et al. |
| 9,345,274 B1 | 5/2016 | Prill |
| 9,498,565 B2 | 11/2016 | Nowroozi et al. |
| 9,539,377 B2 | 1/2017 | Makower et al. |
| D788,293 S | 5/2017 | Eckstein et al. |
| D809,646 S | 2/2018 | Mason et al. |
| 10,039,871 B2 | 8/2018 | Pollen et al. |
| D832,995 S | 11/2018 | Mason et al. |
| 10,398,816 B2 | 9/2019 | Chang et al. |
| 10,625,005 B2 | 4/2020 | Chang et al. |
| D888,225 S | 6/2020 | Askem et al. |
| 10,864,306 B2 | 12/2020 | Fujisaki |
| 10,881,766 B2 | 1/2021 | O'Toole et al. |
| 10,926,011 B2 | 2/2021 | O'Toole et al. |
| 11,260,151 B2 | 3/2022 | O'Toole et al. |
| 11,311,654 B2 | 4/2022 | O'Toole et al. |
| 11,324,866 B2 | 5/2022 | O'Toole et al. |
| 11,357,893 B2 | 6/2022 | O'Toole et al. |
| 11,357,894 B2 | 6/2022 | O'Toole et al. |
| 11,376,352 B2 | 7/2022 | O'Toole et al. |
| 11,413,380 B2 | 8/2022 | O'Toole et al. |
| 2002/0062103 A1 | 5/2002 | Larsson et al. |
| 2002/0193731 A1 | 12/2002 | Myers et al. |
| 2003/0069536 A1 | 4/2003 | Greter et al. |
| 2004/0024351 A1 | 2/2004 | Greter |
| 2004/0056641 A1 | 3/2004 | Myers et al. |
| 2004/0074281 A1 | 4/2004 | Lobdell et al. |
| 2004/0087898 A1 | 5/2004 | Weniger |
| 2004/0127845 A1 | 7/2004 | Renz et al. |
| 2004/0267215 A1 | 12/2004 | Charlez et al. |
| 2005/0219302 A1 | 10/2005 | Vogeley |
| 2005/0228342 A1 | 10/2005 | Yuen |
| 2005/0245860 A1 | 11/2005 | Britto et al. |
| 2006/0122575 A1 | 6/2006 | Wakabayashi |
| 2007/0051172 A1 | 3/2007 | Perinet et al. |
| 2007/0051727 A1 | 3/2007 | Holley, Jr. |
| 2007/0054651 A1 | 3/2007 | Farmer et al. |
| 2007/0135761 A1 | 6/2007 | Cheng et al. |
| 2007/0179439 A1 | 8/2007 | Vogelin et al. |
| 2007/0219486 A1 | 9/2007 | Myers et al. |
| 2007/0228059 A1 | 10/2007 | Karsan |
| 2007/0236584 A1 | 10/2007 | Frost-Ruebling et al. |
| 2008/0009815 A1* | 1/2008 | Grabenkort ............ A61M 1/81 604/74 |
| 2008/0177224 A1 | 7/2008 | Kelly et al. |
| 2008/0262420 A1 | 10/2008 | Dao et al. |
| 2008/0275386 A1* | 11/2008 | Myers .................. A61M 1/067 604/74 |
| 2008/0299517 A1 | 12/2008 | Delaney, II |
| 2009/0281482 A1 | 11/2009 | Baker et al. |
| 2009/0281485 A1 | 11/2009 | Baker et al. |
| 2010/0292636 A1 | 11/2010 | Renz et al. |
| 2011/0004154 A1 | 1/2011 | Van Schijndel et al. |
| 2011/0009824 A1 | 1/2011 | Yodfat et al. |
| 2011/0196291 A1 | 8/2011 | Vischer et al. |
| 2011/0274566 A1 | 11/2011 | Amirouche et al. |
| 2012/0021068 A1 | 1/2012 | Barness et al. |
| 2012/0035951 A1 | 2/2012 | Goetz et al. |
| 2012/0043065 A1 | 2/2012 | Ranne et al. |
| 2012/0072117 A1 | 3/2012 | Loddoch et al. |
| 2012/0072118 A1 | 3/2012 | Mann |
| 2012/0095599 A1 | 4/2012 | Pak et al. |
| 2012/0109083 A1 | 5/2012 | Coulthard et al. |
| 2012/0143879 A1 | 6/2012 | Stoitsev |
| 2012/0165729 A1 | 6/2012 | Cudworth |
| 2012/0220753 A1 | 8/2012 | Gera et al. |
| 2012/0277636 A1 | 11/2012 | Blondheim et al. |
| 2013/0023821 A1 | 1/2013 | Khalil et al. |
| 2014/0031744 A1 | 1/2014 | Chen |
| 2014/0052056 A1 | 2/2014 | Garbez et al. |
| 2014/0142501 A1 | 5/2014 | Clark et al. |
| 2014/0227112 A1 | 8/2014 | Felber |
| 2014/0263611 A1 | 9/2014 | Bauer |
| 2014/0275857 A1 | 9/2014 | Toth et al. |
| 2014/0288466 A1 | 9/2014 | Alvarez et al. |
| 2014/0323962 A1 | 10/2014 | Kooijker et al. |
| 2014/0378895 A1 | 12/2014 | Barack |
| 2015/0157775 A1 | 6/2015 | Hu |
| 2015/0212036 A1 | 7/2015 | Jin et al. |
| 2015/0212037 A1 | 7/2015 | Okazaki et al. |
| 2015/0217036 A1 | 8/2015 | Pollen et al. |
| 2015/0217037 A1 | 8/2015 | Pollen et al. |
| 2015/0283311 A1 | 10/2015 | Alvarez et al. |
| 2015/0314053 A1 | 11/2015 | Furrer et al. |
| 2016/0000980 A1 | 1/2016 | Alvarez et al. |
| 2016/0058928 A1 | 3/2016 | Nowroozi et al. |
| 2016/0058929 A1 | 3/2016 | Medvedev et al. |
| 2016/0082165 A1 | 3/2016 | Alvarez et al. |
| 2016/0082166 A1 | 3/2016 | Guthrie et al. |
| 2016/0135998 A1 | 5/2016 | Riesinger |
| 2016/0151551 A1 | 6/2016 | Felber |
| 2016/0158424 A1 | 6/2016 | Chen et al. |
| 2016/0166745 A1 | 6/2016 | Aalders |
| 2016/0206794 A1 | 7/2016 | Makower et al. |
| 2016/0220743 A1 | 8/2016 | Guthrie et al. |
| 2016/0220745 A1 | 8/2016 | Guthrie et al. |
| 2016/0228625 A1 | 8/2016 | Holtz et al. |
| 2016/0256617 A1 | 9/2016 | Hansen |
| 2016/0271305 A1 | 9/2016 | Kurihara et al. |
| 2016/0287767 A1 | 10/2016 | Simmons et al. |
| 2016/0296681 A1 | 10/2016 | Gaskin et al. |
| 2016/0296682 A1 | 10/2016 | Phillips et al. |
| 2016/0310650 A1 | 10/2016 | Makower et al. |
| 2016/0325031 A1 | 11/2016 | Miller et al. |
| 2017/0021068 A1 | 1/2017 | Gaskin et al. |

(56) References Cited

U.S. PATENT DOCUMENTS

| | | |
|---|---|---|
| 2017/0035951 A1 | 2/2017 | Tanaka |
| 2017/0043065 A1 | 2/2017 | Takeuchi |
| 2017/0072117 A1 | 3/2017 | Kurihara et al. |
| 2017/0072118 A1 | 3/2017 | Makower et al. |
| 2017/0095599 A1 | 4/2017 | Kondo et al. |
| 2017/0112983 A1 | 4/2017 | Thorne et al. |
| 2017/0143879 A1 | 5/2017 | Okaguchi |
| 2017/0173232 A1* | 6/2017 | Chang ............... A61M 1/06 |
| 2017/0173233 A1 | 6/2017 | Tanaka |
| 2017/0216505 A1 | 8/2017 | Kim |
| 2017/0220753 A1 | 8/2017 | Guthrie et al. |
| 2017/0292509 A1 | 10/2017 | Kurihara et al. |
| 2018/0008758 A1* | 1/2018 | Garbez ............. A61M 1/066 |
| 2018/0021490 A1 | 1/2018 | Chang et al. |
| 2018/0021491 A1* | 1/2018 | Rigert ............... A61M 1/062 |
| | | 604/74 |
| 2018/0028733 A1 | 2/2018 | Rigert et al. |
| 2018/0104396 A1* | 4/2018 | Park .................. A61M 1/066 |
| 2018/0110900 A1 | 4/2018 | Korenfeld |
| 2018/0110906 A1 | 4/2018 | Barack |
| 2018/0333523 A1 | 11/2018 | Chang et al. |
| 2018/0361040 A1* | 12/2018 | O'Toole ............. G16H 40/63 |
| 2019/0209748 A1* | 7/2019 | Analytis ............. A61M 1/06 |
| 2019/0365966 A1 | 12/2019 | Bächler et al. |
| 2020/0016307 A1 | 1/2020 | Edelman et al. |
| 2020/0300237 A1 | 9/2020 | Marbet et al. |
| 2021/0030934 A1 | 2/2021 | Zhang |
| 2021/0093761 A1* | 4/2021 | Hwang .............. A61M 39/22 |
| 2021/0170080 A1 | 6/2021 | O'Toole et al. |
| 2021/0196873 A1 | 7/2021 | O'Toole et al. |
| 2021/0196874 A1 | 7/2021 | O'Toole et al. |
| 2021/0196875 A1 | 7/2021 | O'Toole et al. |
| 2021/0196876 A1 | 7/2021 | O'Toole et al. |
| 2021/0205511 A1 | 7/2021 | O'Toole et al. |
| 2021/0205512 A1 | 7/2021 | O'Toole et al. |
| 2021/0205513 A1 | 7/2021 | O'Toole et al. |
| 2021/0205514 A1 | 7/2021 | O'Toole et al. |
| 2021/0205515 A1 | 7/2021 | O'Toole et al. |
| 2021/0205516 A1 | 7/2021 | O'Toole et al. |
| 2021/0205517 A1 | 7/2021 | O'Toole et al. |
| 2021/0205518 A1 | 7/2021 | O'Toole et al. |
| 2021/0228789 A1 | 7/2021 | O'Toole et al. |
| 2021/0268158 A1 | 9/2021 | O'Toole et al. |
| 2023/0111110 A1 | 4/2023 | De Becdelievre et al. |
| 2023/0143842 A1 | 5/2023 | O'Toole et al. |
| 2023/0158215 A1 | 5/2023 | O'Toole et al. |

FOREIGN PATENT DOCUMENTS

| | | |
|---|---|---|
| DE | 3311982 C2 | 12/1986 |
| DE | 19750620 A1 | 6/1999 |
| EP | 0503280 A2 | 9/1992 |
| EP | 1586340 A2 | 10/2005 |
| EP | 1430918 B1 | 5/2008 |
| EP | 2436277 A1 | 4/2012 |
| EP | 2502640 A1 | 9/2012 |
| EP | 2210628 B1 | 2/2013 |
| EP | 1404393 B1 | 12/2014 |
| EP | 2077868 B1 | 7/2016 |
| EP | 1263487 B2 | 11/2016 |
| EP | 3482782 A1 | 5/2019 |
| GB | 2435617 B | 3/2008 |
| GB | 2473022 B | 12/2011 |
| GB | 2499248 B | 4/2014 |
| JP | H 11-178917 A | 7/1999 |
| JP | 2000-350527 A | 12/2000 |
| JP | 2007501673 A | 2/2007 |
| JP | 2013-545519 A | 12/2013 |
| JP | 2014529312 A | 11/2014 |
| JP | 2014-532498 A | 12/2014 |
| JP | 2016010524 A | 1/2016 |
| JP | 2016514516 A | 5/2016 |
| JP | 2016-524490 A | 8/2016 |
| JP | 2016-526396 A | 9/2016 |
| JP | 2017-503552 A | 2/2017 |
| JP | 2017509379 A | 4/2017 |
| RU | 2344380 C1 | 1/2009 |
| RU | 2441367 C2 | 2/2012 |
| WO | WO-9420158 A1 | 9/1994 |
| WO | WO 2004/108184 A2 | 12/2004 |
| WO | WO-2005079441 A2 | 9/2005 |
| WO | WO-2005114113 A2 | 12/2005 |
| WO | WO-2005114116 A1 | 12/2005 |
| WO | WO-2005114113 A3 | 3/2006 |
| WO | WO-2009134271 A1 | 11/2009 |
| WO | WO 2013/064852 A1 | 5/2013 |
| WO | WO 2014/160614 A1 | 10/2014 |
| WO | WO-2015081459 A1 | 6/2015 |
| WO | WO-2015116749 A1 | 8/2015 |
| WO | WO-2015120321 A1 | 8/2015 |
| WO | WO-2015150225 A1 | 10/2015 |
| WO | WO-2015174330 A1 | 11/2015 |
| WO | WO 2016/006458 A1 | 1/2016 |
| WO | WO-2016002606 A1 | 1/2016 |
| WO | WO-2016006494 A1 | 1/2016 |
| WO | WO-2016006496 A1 | 1/2016 |
| WO | WO-2016007560 A1 | 1/2016 |
| WO | WO-2016007561 A1 | 1/2016 |
| WO | WO-2016010524 A1 | 1/2016 |
| WO | WO-2016014469 A1 | 1/2016 |
| WO | WO-2016014488 A1 | 1/2016 |
| WO | WO 2016/025405 A1 | 2/2016 |
| WO | WO-2016024558 A1 | 2/2016 |
| WO | WO-2016039083 A1 | 3/2016 |
| WO | WO-2016104673 A1 | 6/2016 |
| WO | WO-2016164853 A1 | 10/2016 |
| WO | WO-2017061349 A1 | 4/2017 |
| WO | WO-2017108555 A1 | 6/2017 |
| WO | WO-2017139480 A1 | 8/2017 |

OTHER PUBLICATIONS

Extended European Search Report issued in European Application No. 22174446.9, dated Oct. 11, 2022; 26 pages.

GB Search Report for , dated Nov. 29, 2017, issued in priority GB Application No. GB1709564.7.

GB Search Report, dated Nov. 15, 2017, issued in priority GB Application No. GB1709561.3.

GB Search Report, dated Nov. 28, 2017, issued in priority GB Application No. GB1709566.2.

International Search Report issued in PCT/GB2018/051659 dated Dec. 4, 2018, 9 pages.

Japanese Search Report issued in Japanese Application No. 2020-519188, dated Jun. 24, 2022, 20 pages.

The Best Hands-Free Breast Pumps, posted at healthline.com, earliest date posted on Aug. 24, 2020, [online], acquired on Oct. 30, 2021, Available on internet. url:https://www.healthline.com/health/parenting/breast-feeding/best-hands-free-breast-pumps#Best-hands-free-breast-pumps (Year: 2020).

Whisper Wear Hands-Free Breast Pump, Model:WWPMP01, UserGuide,pp. 1-20 , Distributed with product atleast as early as 2007 (seehttps://web.archive.org/web/20070621162539/http://www.whisperwear.com/pump_single.html).

International Search Report issued in International Application No. PCT/GB2021/050764, dated Jul. 6, 2021, 5 pages.

Amended Complaint in *Shenzhen Root Technology Co., Ltd.* v. *Chiaro Technology, Ltd.*, WDWA-2-23-cv-00631, filed Jun. 2, 2023; 24 pages.

\* cited by examiner

|  | Lima Single Profile | Lima Double Profile | Power Motor |
|---|---|---|---|
| STIMULATION |  |  |  |
| Level 1 | -60 | -35 | 45% |
| Level 2 | -85 | -55 | 50% |
| Level 3 | -105 | -65 | 50% |
| Level 4 | -115 | -70 | 55% |
| Level 5 | -135 | -85 | 60% |
| Level 6 | -170 | -110 | 65% |
| Level 7 | -190 | -125 | 65% |
| Level 8 | -210 | -140 | 70% |
| level 9 | -230 | -155 | 70% |
| level 10 | -250 | -170 | 70% |
| EXPRESSION |  |  |  |
| Level 1 | -60 | -35 | 45% |
| Level 2 | -90 | -55 | 50% |
| Level 3 | -130 | -80 | 60% |
| Level 4 | -170 | -110 | 65% |
| Level 5 | -200 | -130 | 65% |
| Level 6 | -240 | -160 | 70% |
| Level 7 | -275 | -190 | 73% |
| Level 8 | -310 | -220 | 75% |
| level 9 | -340 | -260 | 80% |
| level 10 | -365/350 | -300 | 80% |

FIGURE 28

WEARABLE BREAST PUMP SYSTEM

CROSS-REFERENCE TO RELATED APPLICATIONS

The present application is a continuation of U.S. application Ser. No. 17/907,347, filed Sep. 26, 2022, which is the national stage of International Application No. PCT/GB2021/050764, filed Mar. 26, 2021, which claims priority to GB Application No. 2004395.6, filed Mar. 26, 2020, each of which is incorporated herein by reference in its entirety.

BACKGROUND OF THE INVENTION

1. Field of the Invention

The field of the invention relates to a wearable breast pump system.

2. Description of the Prior Art

A breast pump system is a mechanical or electro-mechanical device that extracts milk from the breasts of a lactating woman.

Most portable breast pump solutions that include a discreet design are not readily affordable for most parents. There is a need for a design of a wearable breast pump system with a sleek and discreet design as well as a lower price point.

A fully integrated wearable breast pump system is described in WO2018229504A1. The wearable breast pump system includes a housing shaped to fit inside a bra. The housing includes an air-pump that drives a diaphragm to generate negative air pressure. The diaphragm is seated on a diaphragm holder that is positioned away from a side of a breast shield flange.

A compact and hands-free human breast milk collection device that fits into a mother's existing nursing or standard brassiere is shown in the system of US20080262420A1. The hands-free collection device connects to an external regular pump via a vacuum hose that is also configured to apply a vacuum pressure to the internal volume of the collection device. The vacuum hose attaches to a stem located at a fixed position on the top exterior surface of the collection device. The position of the stem is chosen so that the pump will not suction breast milk into the external pump. Because it would be inconvenient and difficult to connect the vacuum hose to the stem located at the top of the device after the device has been placed on the breast, the vacuum hose has to be properly connected to the stem before the milk collection device is being placed on the breast.

A breast milk collection device is also shown in the system of US20180008758A1. The collection device attaches to a vacuum tube via an opening also located at a fixed position on the rim of the exterior surface of the collection device. The opening communicates with an interior chamber including an inflatable/deflatable flexible barrier that allows vacuum pressure to be applied to a breast. The flexible barrier housing that encloses the flexible barrier has an oval cone like shape and is located at the top of the collection device. Disadvantageously, the position of the flexible barrier obstructs the line of sight to the interior of the collection device and to the nipple.

Wearable hands free breast pumps have entered the market, such as the Freemie cups system. The Freemie cup includes a flexible barrier that sits on top of the cup, thereby obstructing the view of the interior of the cup and of the nipple. Further, the cup is also made of a fairly opaque material, making it difficult to have a clear view of the interior of the device and of the nipple and to achieve a correct nipple alignment.

In view of the above, there is a need for an improved way to provide an easy and flexible connection between a suction tube and a wearable milk collection device. There is also a need to provide an unobstructed view of the interior chamber of the wearable milk collection device, in order to achieve a correct nipple alignment and to ensure the system is properly operating, such that milk is entering the interior of the device.

SUMMARY OF THE INVENTION

The invention is a breast pump system comprising at least one wearable milk collection hub connected via an air line to a combined external air pump and control unit. The milk collection hub(s) each comprise: a breast shield made up of a breast flange and a nipple tunnel; a flexible diaphragm that is configured to prevent milk from reaching the external air pump; an outer shell that is removably attachable to the breast shield, such that the breast shield and outer shell, when attached, form a vessel for collecting milk, and the front face of the outer shell includes a curved portion; a diaphragm cap that is configured to be secured over the diaphragm, and forms part of the front face or forward facing part of the outer shell, and includes a port connected to the air line.

This arrangement enables the air line to be connected to the front face of the outer shell of the milk collection hub; prior art devices position the diaphragm and air line on the top of the milk collection hub, which obscures the users view down into device, which in turn makes correct nipple positioning difficult. By having a diaphragm cap that forms part of the front face of the outer shell, the user's view down into the device is not obscured by a diaphragm that sits over the nipple; correct nipple positioning is easier to achieve.

In one implementation, the diaphragm cap can be rotated against the outer shell to adjust the position of the air port and hence the position and direction of the port and the air line connected to the port; this enables the user to readily adjust the position of the air line so that it lies comfortably under a bra or other clothing. The diaphragm cap may also be removable from the outer shell; then, the user can place the hub on the breast without the diaphragm cap, and without the inconvenience of an air line connected to the air port. Once a proper nipple alignment is achieved, the diaphragm cap and connected air line can then easily be attached back onto the outer shell of the milk collection hub.

BRIEF DESCRIPTION OF THE FIGURES

Aspects of the invention will now be described, by way of example(s), with reference to the following Figures, which each show features of a wearable breast pump system that implements the invention:

FIG. 28 shows a table listing different examples of vacuum levels.

INDEX

Figure 1A:
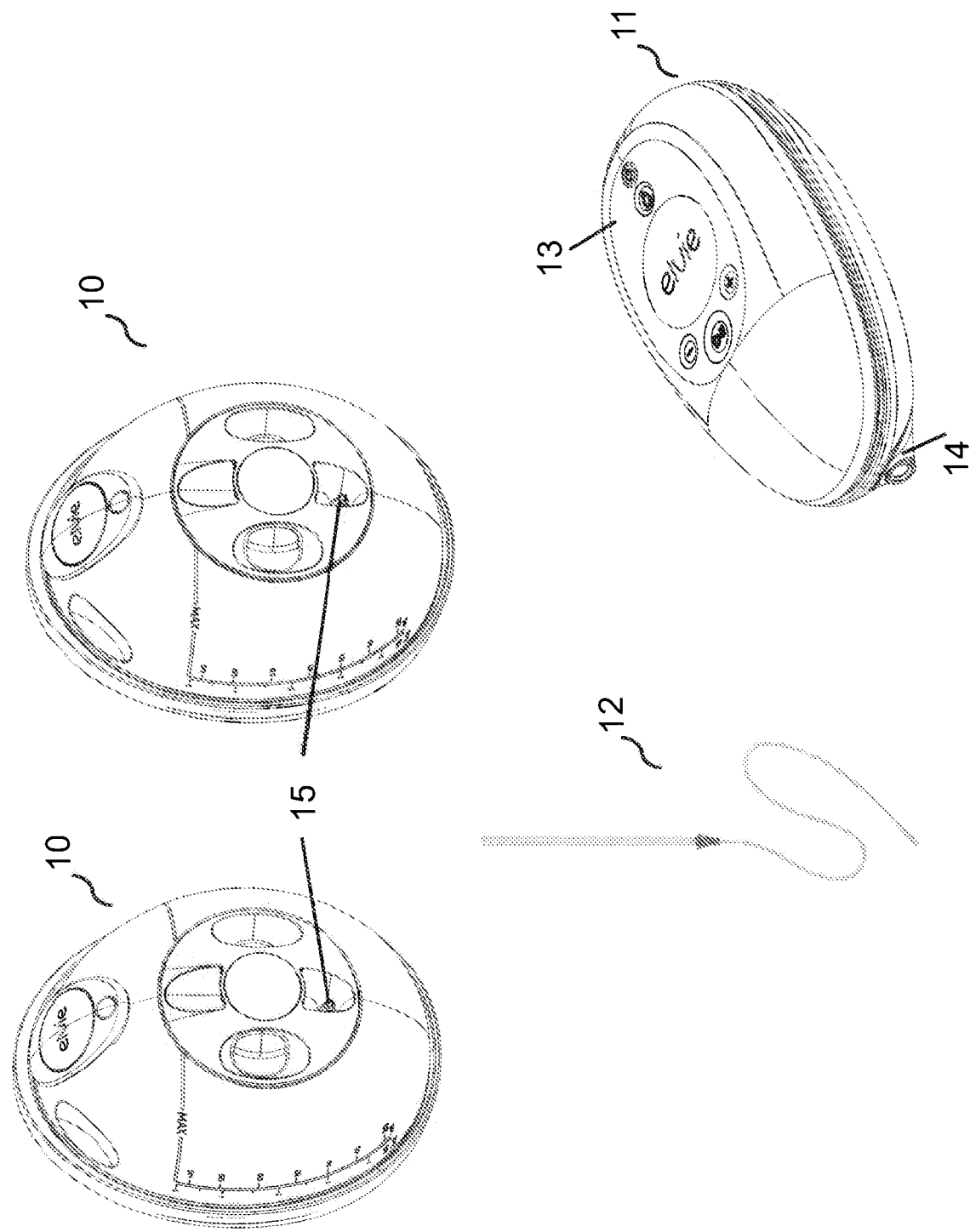
FIG. 1A shows a wearable breast pump system, made up of a pair of milk collection hubs, an air line and a separate combined control and air pump unit that is external to the milk collection hubs.

| | |
|---|---|
| Air line leading to milk collection hub | 1 |
| Air line leading to milk collection hub | 2 |
| Air line leading from combined control and air pump unit | 3 |
| Milk collection hub | 10 |
| Combined control and air pump unit | 11 |
| Air tube connection component | 12 |
| User interface on the control and air pump unit | 13 |
| Air port or hole in the control and air pump unit | 14 |
| Air port or hole in the diaphragm cap | 15 |
| Outer shell of a milk collection hub | 20 |
| Breast shield | 21 |
| Diaphragm cap | 22 |
| Cover to milk opening | 23 |
| Milk quantity scale on the shell | 24 |
| Finger grip features | 30 |
| Nipple tunnel part of the breast shield | 31 |
| Flange of the breast shield | 32 |
| Guide lines on the breast shield | 33 |
| Milk hole in the nipple tunnel | 41 |
| Milk non-return valve | 51 |
| Second milk hole | 52 |
| Diaphragm housing | 53 |
| Diaphragm housing, annular rear wall | 54 |
| Diaphragm housing, cylindrical outer wall | 55 |
| Diaphragm housing, cylindrical inner wall | 56 |
| Diaphragm housing, front wall | 57 |
| Diaphragm | 61 |
| Seal between breast shield and outer shell | 62 |
| Diaphragm, annular rear wall | 63 |
| Diaphragm, cylindrical outer wall | 64 |
| Diaphragm, cylindrical inner wall | 65 |
| Diaphragm, front wall | 66 |
| Central axis through the nipple tunnel | 81 |
| Pressure chamber in a relaxed state | 82 |
| Pressure chamber under maximum negative pressure | 83 |
| Pair of chambers in the diaphragm cap | 84 |
| Illustration of end-user breast area | 85 |
| Rigid pressure chamber part | 91 |
| Ball bearings | 100 |
| Cross section in relaxed state | 101 |
| Cross section at mid point | 102 |
| Cross section at maximum pressure | 103 |
| Milk pouring opening | 111 |
| Flat portion of the diaphragm cap | 120 |
| Dual function pump/pause button | 130 |
| Power on/off button | 131 |
| Button to switch the pumping profile | 132 |
| Pressure decrease button | 133 |
| Pressure increase button | 134 |
| Pressure level visual indicator LEDs | 135 |
| Pumping profile visual indicator LEDs | 136 |
| Battery status LED | 137 |
| USB-C charging socket | 138 |
| Chassis | 140 |
| Upper case | 151 |
| Lower case | 152 |
| PCB | 153 |
| Air pump unit subsystem | 154 |
| Rechargeable battery | 155 |
| Pump unit | 161 |
| Solenoid air bleed valve | 162 |
| Sound attenuating motor mount | 163 |
| Airflow block | 164 |
| Solenoid foam cap | 165 |
| Sound valve | 166 |
| Sound valve cap | 167 |
| Solenoid valve inlet | 171 |
| Solenoid valve outlet | 172 |
| Seal member | 173 |
| Motor exhaust | 181 |
| Tube wrap accessory | 241 |
| Battery accessory | 242 |
| Milk drawn from nipple into chamber | 251 |
| Removable waistband clip | 261 |
| Tube splitter | 261 |
| Bung or stopper in the tube splitter | 262 |
| O-ring | 290 |
| Control unit and o-ring in portrait mode | 291 |
| Control unit and o-ring in landscape mode | 292 |
| First phase of pumping cycle (pumping time) | P |
| Second phase of pumping cycle (bleed time) | B |

DETAILED DESCRIPTION

Figure 1B:
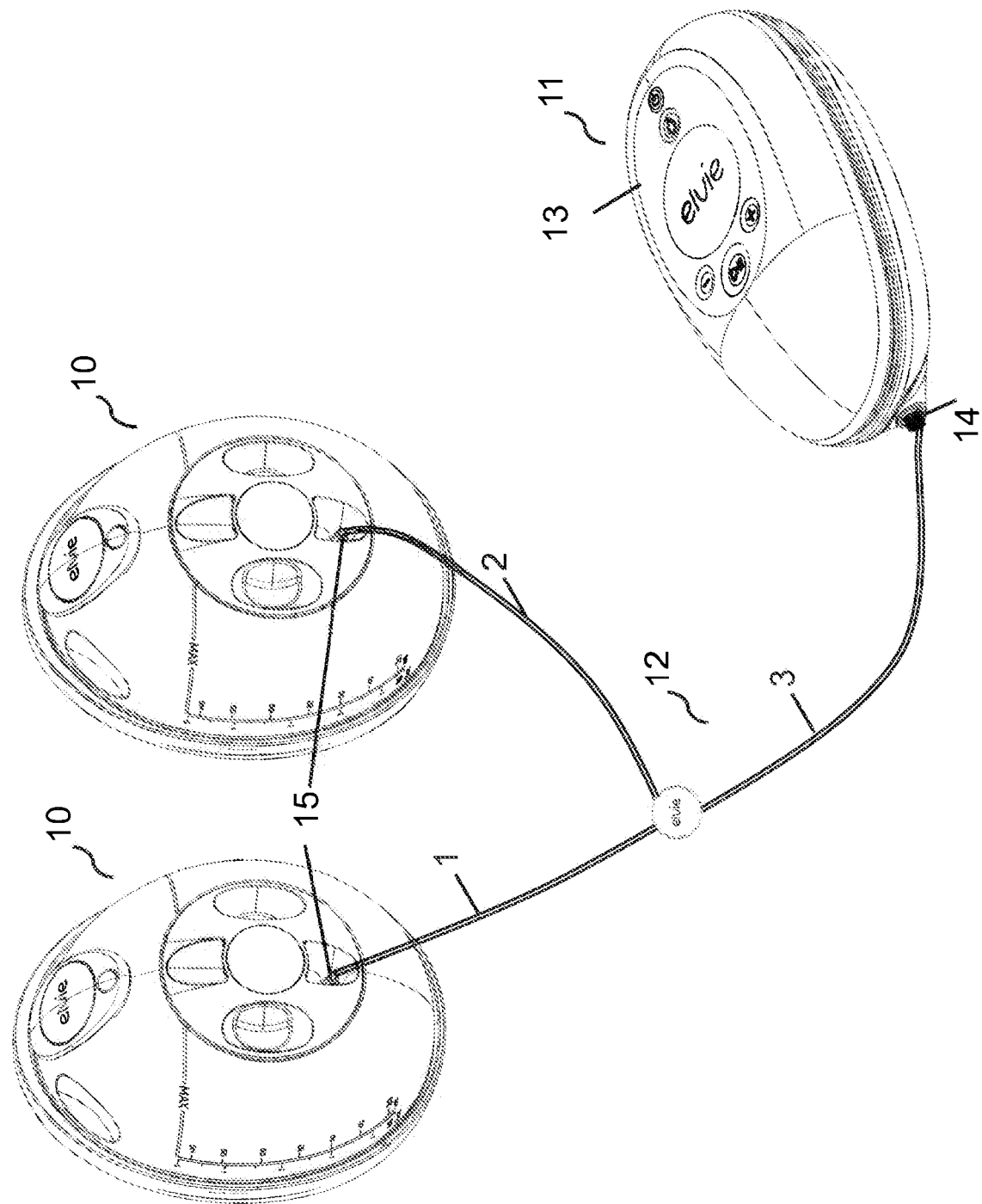
FIG. 1B shows the wearable breast pump system with the milk collection hubs connected via the air line to the combined control and air pump unit.

An implementation of the invention is a breast pump system for extracting and collecting breast milk. The system comprises a pair of milk collection hubs 10, a combined control and air pump unit 11, and an air tube connection component 12, as shown in FIG. 1A. In normal use, as shown in FIG. 1B, air tubes 1, 2 connect each milk collection hub 10 to the air tube connection component 12; the air tube connection component 12 connects air tubes 1, 2 to a single air tube 3, that in turn leads to the control and air pump unit 11.

The milk collection hubs may also be connected to any external control and air pump unit, including any external regular electric or manual control and air pump unit.

An intended use case involves the user placing either one or two milk collection hubs 10 onto their breast(s), connecting one or both collection hubs to the combined control and air pump unit 11 via the air tubes 1, 2 and 3 and the tube connection component 12.

The user controls the device using a user interface 13 located on the control unit 11. Starting the breast pump system, via the user interface 13, activates an air suction pump within the control and air pump unit 11 (also referred as control unit). An air port or hole 14 on the control and air pump unit 11 connects to a tube 3 which splits via a tube splitter in the air tube connection component 12 into two tubes 1, 2, which then deliver suction to the milk collection hubs 10 via air ports or holes 15 in each milk collection hub 10. When the pump in unit 11 is activated, negative air pressure is created between the control unit 11 and the milk collection hub(s) 10, thereby applying negative pressure to the nipple, drawing milk from the breast, and collecting it inside the milk collection hubs 10.

The breast pump system can be operated using either one (single pumping) or two (double pumping) milk collection hubs 10. The breast pump system can generate pressures in the range of 150 to 350 mmHg depending on the level of stimulation selected by the user.

Figure 2:
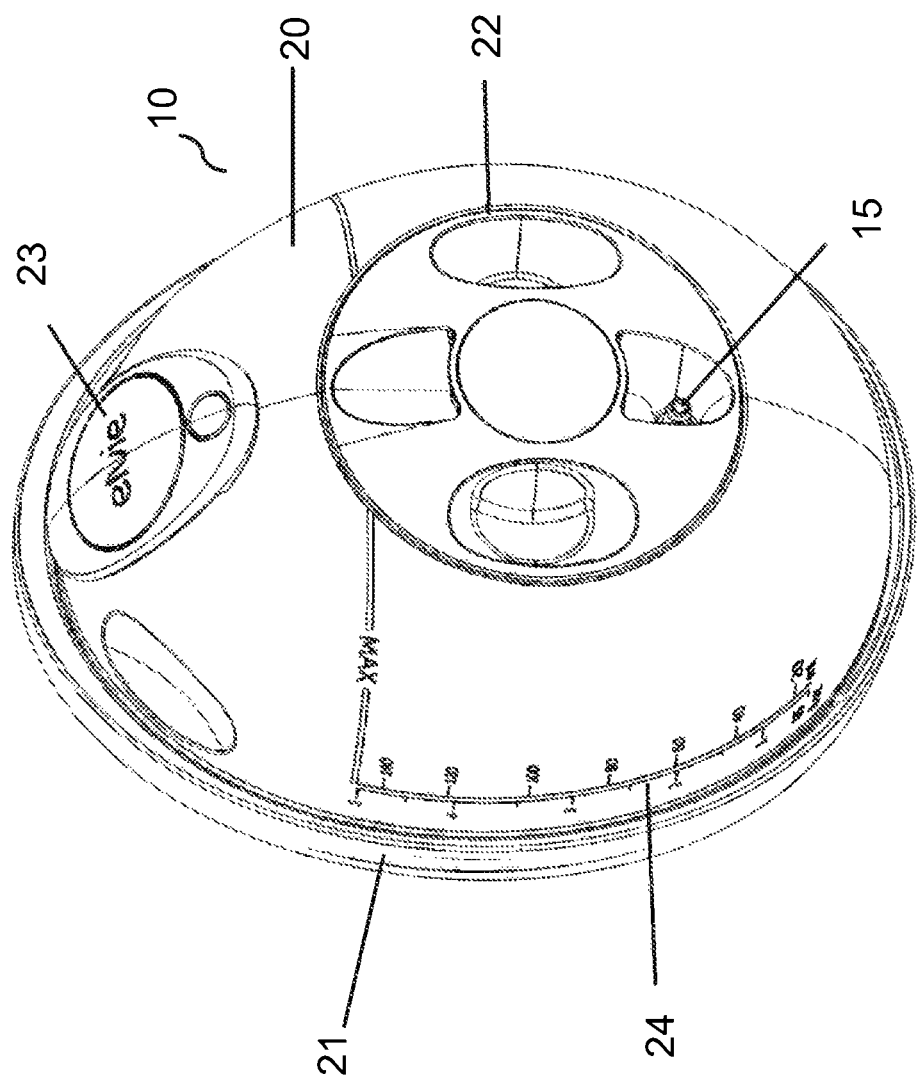
FIG. 2 shows a perspective front view of a milk collection hub.
Figure 3:
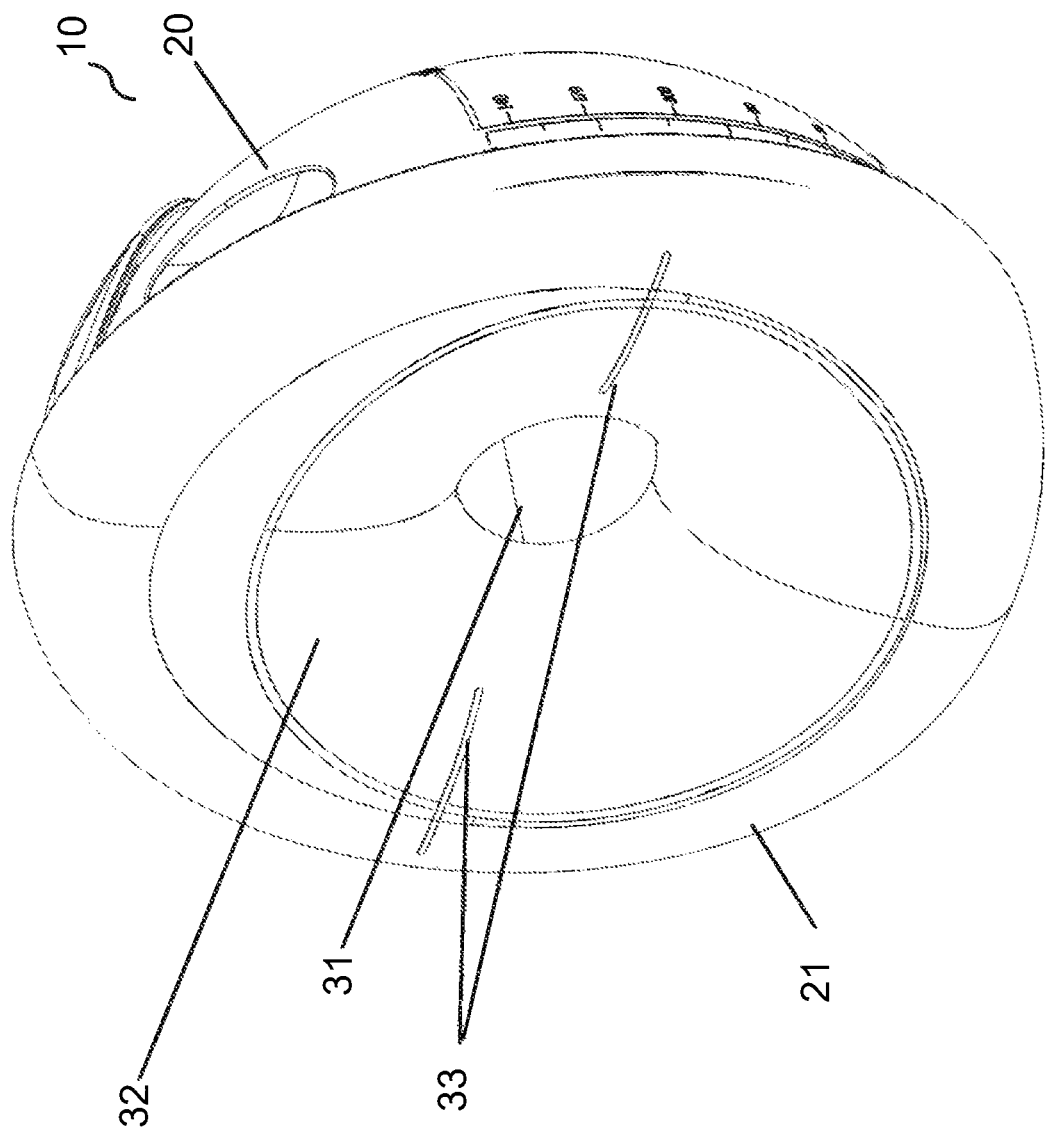
FIG. 3 shows a perspective rear view of a milk collection hub.

FIGS. 2 and 3 show perspective views of a milk collection hub. The milk collection hubs 10 are both identical and are configured to be discreet and to be comfortably held inside a bra, with the outer shell 20 having a curved shape that is configured to contact the inner surface of the bra. The outer shell 20 fits or latches onto a breast shield 21 that forms the rear surface of the hub 10. The breast shield 21 is made up of a breast flange 32 and a nipple tunnel 31; the interior volume between the outer shell 20 and the breast shield 21 defines a chamber in which milk is collected. The breast flange 32 contacts the user's breasts. The outer shell 20 is directly removable from the breast shield in normal use or normal dis-assembly to enable cleaning of the interior volume in which milk is collected.

The outer shell 20 also includes a removable diaphragm cap 22 that covers and seals a diaphragm located inside the milk collection hub. The diaphragm cap 22 is located at the front of the outer shell 20, and forms a central region on the front surface of the outer shell 20. The diaphragm cap 22 includes the air port or hole 15 which provides the air connection to the control unit 11 via a tube. Because the diaphragm cap 22 is positioned at the front of the outer shell 20, it does not block the user's view down through the transparent outer shell 20 into the interior of the milk collection hub; it hence enables the user to see whether the collection hub 10 is correctly positioned on a breast and whether milk is being successfully expressed into the collection hub 10.

The diaphragm cap 22 is easily removable with one hand from the outer shell 20 of the hub in normal use or normal disassembly. Because the air line 1, 2 is connected to the air hole 15 in the diaphragm cap 22, removing the diaphragm cap 22 from the outer shell 20 provides a robust, easy, quick release of the suction connection between the hub 10 and the control unit 11, and, similarly, a robust, easy, quick installation of the suction connection between the hub 10 and the control unit 11. Generally, air lines 1, 2 remain fixed to their respective diaphragm cap 22, so the user does not have to worry about the potentially difficult process of attaching the air lines to the air port 15 in each collection hub 10.

The removable diaphragm cap 22 can be rotated against outer shell 20 to adjust the position of the air port on the outer shell and hence the position and direction of the air lines 1, 2; this enables the user to readily adjust the position of the air lines 1, 2 so that they lie comfortably under a bra or other clothing. The user can place the hub 10 on the breast without the diaphragm cap and without the inconvenience of an air tube 1, 2 connected to the air port 15. Once a proper nipple alignment is achieved, the diaphragm cap 22 and connected tube can easily be attached on the hub 10.

In FIG. 3, the breast shield 21 includes a nipple tunnel 31 shaped to receive a nipple and a flange 32. Preferably, the breast shield 21 including the flange 32 and the nipple tunnel 31 is a single piece item made of a single moulding with a single smooth internal surface. There are no joins along the nipple tunnel; joins may aggravate the delicate nipple tissue as the nipple extends and contracts during pumping.

The breast shield 21 may be configured to slide onto the outer shell using a single push action. The breast shield 21 and outer shell 20 may also attach using magnets.

Preferably, the breast shield 21, and the outer shell 20 and the diaphragm cap 22 are all substantially rigid and optically clear or substantially transparent, e.g. in order to provide an unobstructed view of the nipple and the inside of the hub 10. The breast shield 21, the diaphragm cap 22 and the outer shell 20 may for example all be made substantially of clear, rigid, dishwasher-safe material such as polypropylene, or a polycarbonate, or a co-polyester like Tritan™, or include sections of those materials sufficient to enable the user to clearly see inside the milk collection hub 10. Being dishwasher-safe is important as it enables these components to all be easily cleaned in a normal dish-washing cycle. This also allows different components of the wearable breast pump system to be easily washed and/or sterilised. This rigidity and transparency helps achieve correct nipple alignment when placing the entire milk collection hub 10 onto the breast, as well as to enable the user to readily check whether the alignment is maintained while pumping. Milk collection hubs made of very flexible silicone can be harder to correctly position on breast. The nipple tunnel is also clearly visible to the user through the substantially transparent walls of the hub 10, further ensuring that the spacing between the nipple and the side walls of the nipple tunnel 31 is correctly maintained while pumping.

During a pumping session, the user is also able to view the inside of the milk collection hub 10 and is able to ensure milk is being expressed inside the hub 10 and have an indication of the level of collected milk inside the hub. A scale 24 located on the outer shell 20 indicates the volume of milk inside the hub 10.

Figure 8:
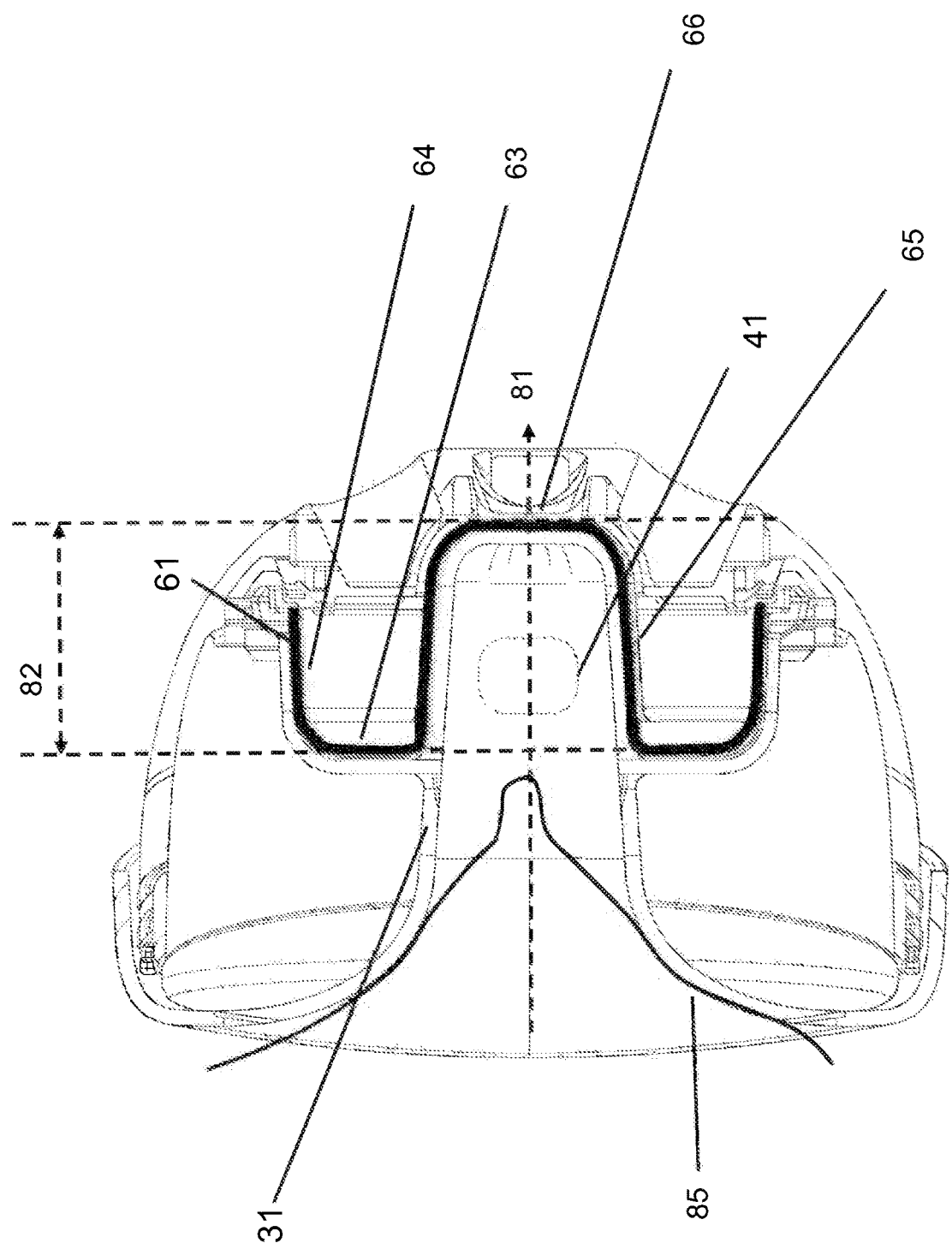
FIG. 8 shows a cross section of a milk collection hub in a relaxed state.

The breast shield 21 may also include guide lines 33 running parallel to the sides of the breast shield in order to help with nipple alignment; these guide lines 33 are designed to be positioned generally horizontally in use, and to be easily seen by the user when looking down at the breast shield 21 when positioned on breast; the lines enable the user to correctly position the breast shield 21 so that the nipple is positioned generally along the centre-line leading through the nipple tunnel (e.g. central axis 81 shown in FIG. 8).

The outer shell also includes a milk pouring opening which can be closed using a removable part 23 to cover the milk pouring opening during pumping and general handling.

The breast shield 21 and/or outer shell 20 may be made of a substantially rigid polypropylene material, or a polycarbonate or a co-polyester material such as the Tritan material that is optically clear and dishwasher safe. The material may be particularly chosen as a balance of cost and acceptable achievable transparency.

Figure 4:
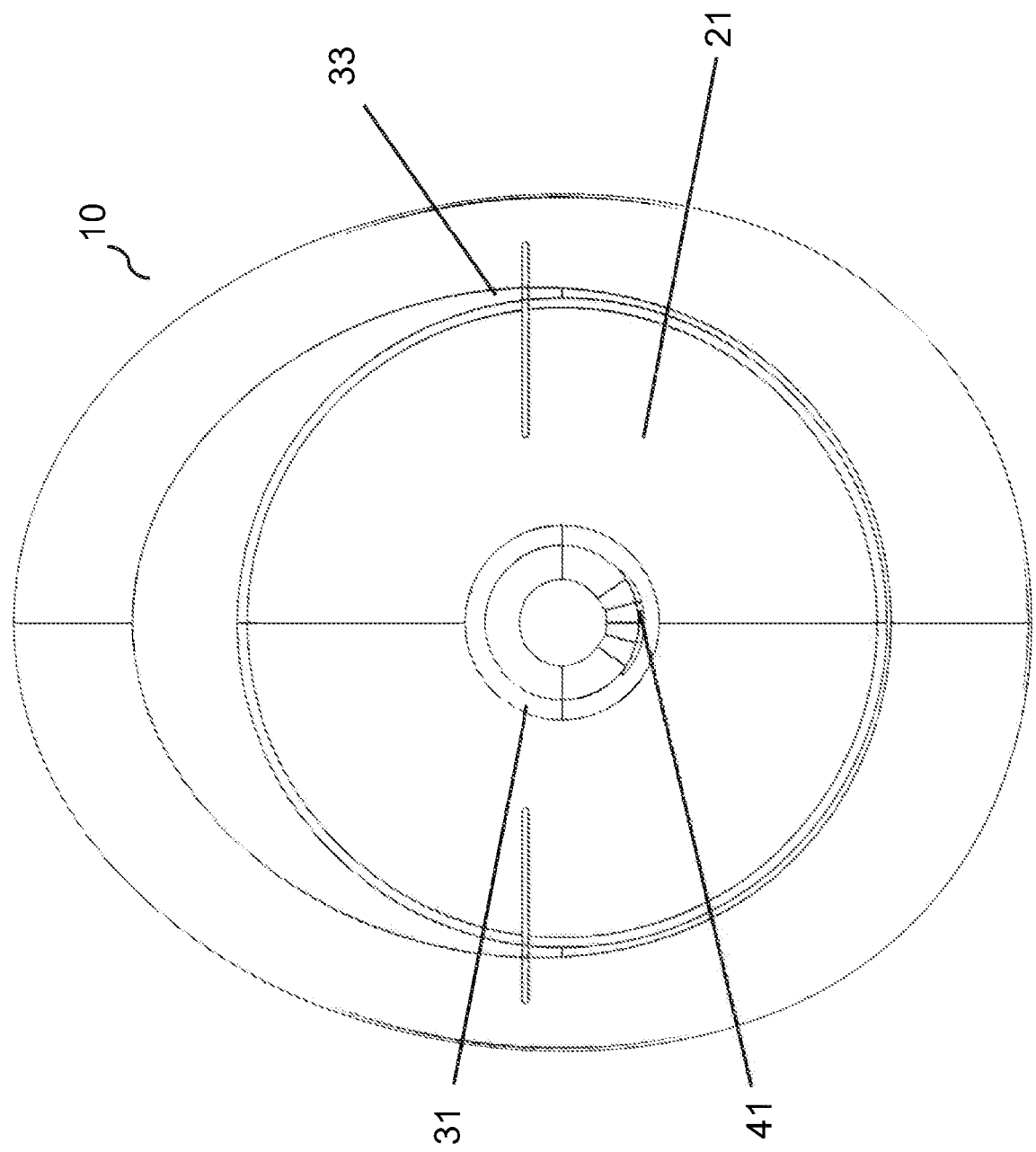
FIG. 4 shows a back view of the milk collection hub.

FIG. 4 shows a back view of the milk collection hub. As shown, the nipple tunnel 31 includes a milk hole 41 through which expressed milk flows onto the milk collection hub. Guide lines 33 are positioned above the central axis of the nipple tunnel 31 and are not aligned with that central axis; this compensates for the slight parallax arising when viewing the guide lines 33 and nipple from above.

Figure 5:
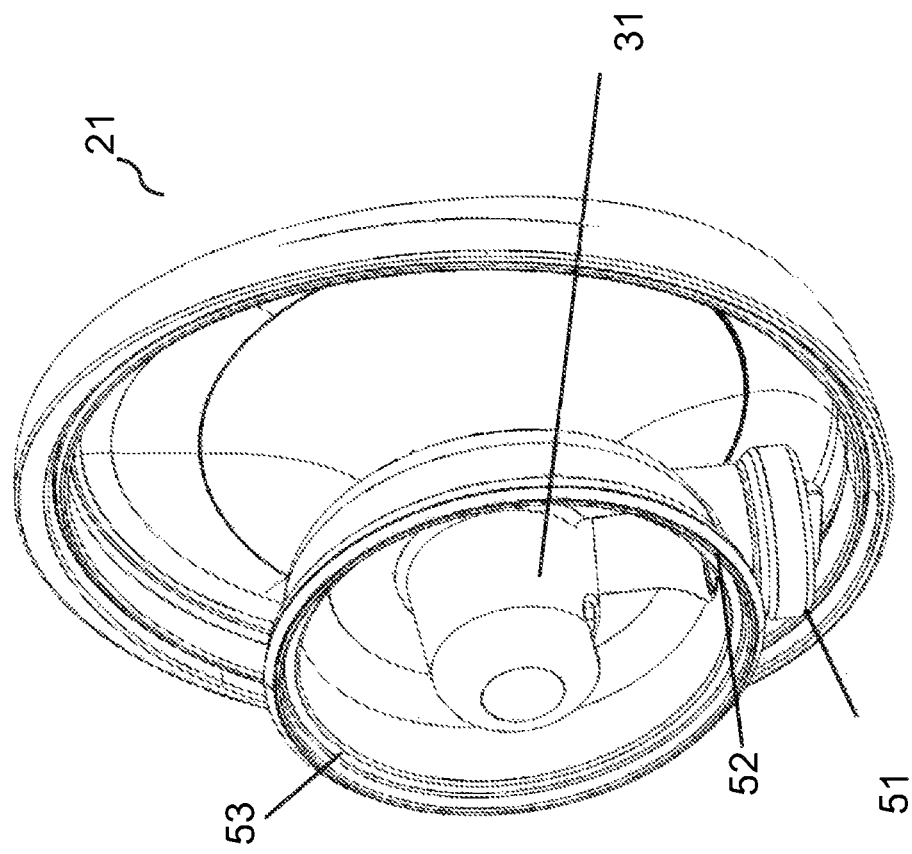
FIG. 5 shows a perspective view of the milk collection hub without the outer shell and without the diaphragm.

FIG. 5 shows a perspective view of the one-piece, rigid breast shield 21 but without the outer shell and without the diaphragm. Breast shield 21 includes an annular diaphragm housing 53; diaphragm housing 53 has an outer, approximately cylindrical side wall 55 that is generally parallel to the nipple tunnel 31, and a generally concentric, approximately cylindrical inner side wall 56 that forms the outer wall of the nipple tunnel 31. Diaphragm housing 53 has a front wall 57 that forms the end of the nipple tunnel; it also has an annular rear wall 54 that joins the concentric inner wall 56 and the outer wall 55.

FIG. 8 provides a cross-section showing these features. A flexible membrane 61 (see FIGS. 6-9 and FIGS. 13A and 13B) sits flush against these walls of the annular diaphragm housing 53 in the relaxed state (i.e. when no negative air pressure is applied) and hence has a similar shape, with a generally cylindrical outer membrane wall 64 that sits flush against housing cylindrical outer wall 55; a concentric inner membrane wall 65 that sits flush against housing cylindrical inner wall 56; a front wall 66 that sits over the end of the housing front wall 57 that forms the end of the nipple tunnel; and an annular rear wall 63 that sits flush against the diaphragm housing rear wall 54.

Diaphragm cap 22 sits over the flexible diaphragm or membrane 61 and a negative pressure chamber is hence formed between diaphragm cap 22 and one side of the flexible diaphragm 61. The diaphragm 61 hence moves within an air-pump chamber formed on one side by the diaphragm housing 53 and on the other side by the diaphragm cap 22; flexible diaphragm 61 is pulled forwards, along the direction of central axis 81, moving through this negative pressure chamber when suction is applied. As the flexible diaphragm 61 is pulled forwards, it creates a low air pressure region on the other side of the flexible diaphragm 61, i.e. the side between the flexible diaphragm 61 and the diaphragm housing 53. This in turn reduces the air pressure inside the nipple tunnel 31, since milk hole 41 in the nipple tunnel 31 ensures air pressure equivalence between the inside of the nipple tunnel 31 and the inside of the diaphragm housing 53; the pressure reduction draws the nipple forward and causes milk to be expressed from the nipple. Milk passes through the milk hole 41 of the nipple tunnel 31, and then passes through a second milk hole or opening 52 located on the diaphragm housing 53, and then flows inside the collection hub via a non-return valve 51 that is mounted on the second milk hole or opening 52. The non-return valve enables milk to pass into the milk container in one direction.

Note that the diaphragm housing 53, and hence the diaphragm 61, is placed towards the end of the nipple tunnel 31, away from the breast shield 21. Diaphragm 61 in fact extends over the end of nipple tunnel 31. This structure has the benefit of giving the user a clearer view down through the nipple tunnel 31 when positioning the nipple inside the nipple tunnel 31: if the diaphragm housing 53 were closer to the breast shield 21, then that view would be blocked. The downside however is that the milk collection hub 10 is not compact in the direction of the nipple tunnel and is shaped to fit inside an inner portion of a bra.

Preferably, the non-return valve is removable for easy cleaning.

When the outer shell 20 is fitted on the breast shield 21, the collection hub forms a vessel in which milk is collected after it passes through the non-return valve with a capacity to collect approximately 5 fluid ounces (148 ml).

The hub also includes a vent hole located for example at the top of the outer shell such that atmospheric pressure is maintained inside the vessel, even during negative pressure cycles.

Figure 6:
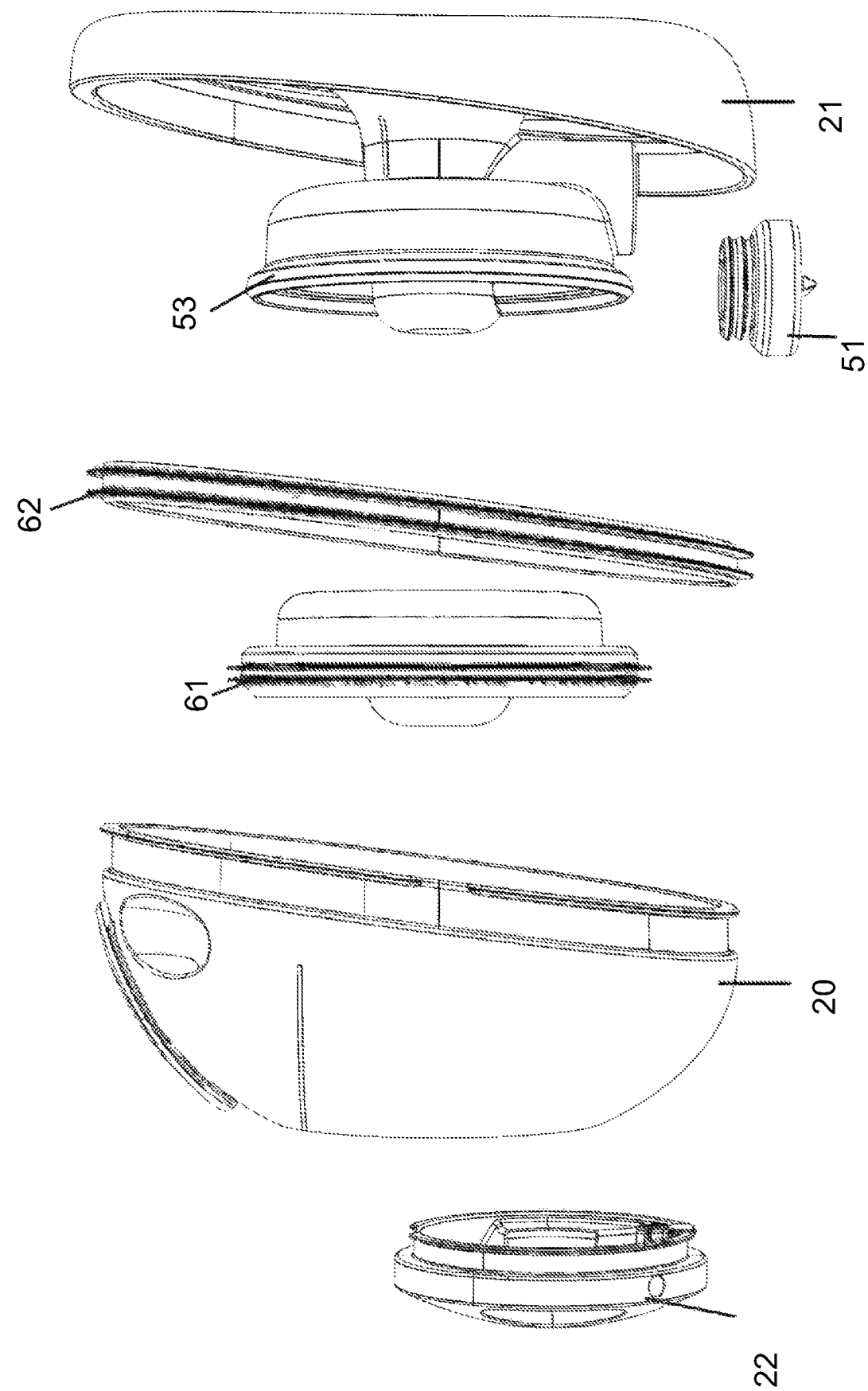
FIG. 6 shows an exploded view of the milk collection hub.

FIG. 6 shows an exploded view of the milk collection hub 10. In this example, the wearable milk collection hub 10 comprises the following user-removable parts: the breast shield 21, the outer shell 20, the diaphragm 61 and the diaphragm cap 22. The diaphragm cap 22 fits over with an air-tight seal to the flexible diaphragm 61. An air tight seal between the breast shield 21 and outer shell 20 is provided by a removable seal member 62.

The flexible diaphragm 61 may either be fully removable from the hub 10 or may form an integral part of the outer shell 20. When it is removable, it push-fits into the outer shell 20, forming an air and liquid tight seal. When it is an integral part of the outer shell, the flexible diaphragm 61 is typically laser welded at its single outer, circular edge, to a single, circular edge in the outer shell 20.

As noted above, the breast shield 21 includes a diaphragm housing portion 53, in which the flexible diaphragm 61, can move in and out, when assembled. The diaphragm housing portion 53 includes an air hole that transfers negative air pressure to the nipple tunnel 31; this may be the milk hole 41 in the nipple tunnel 31 or another hole (not shown). The diaphragm 61 flexes when negative air pressure is applied to it by the external air pump unit subsystem located in the control unit and transfers negative air-pressure to pull the breast and/or nipple against the breast shield and apply suction to the nipple, to cause milk to be expressed.

Figure 7:
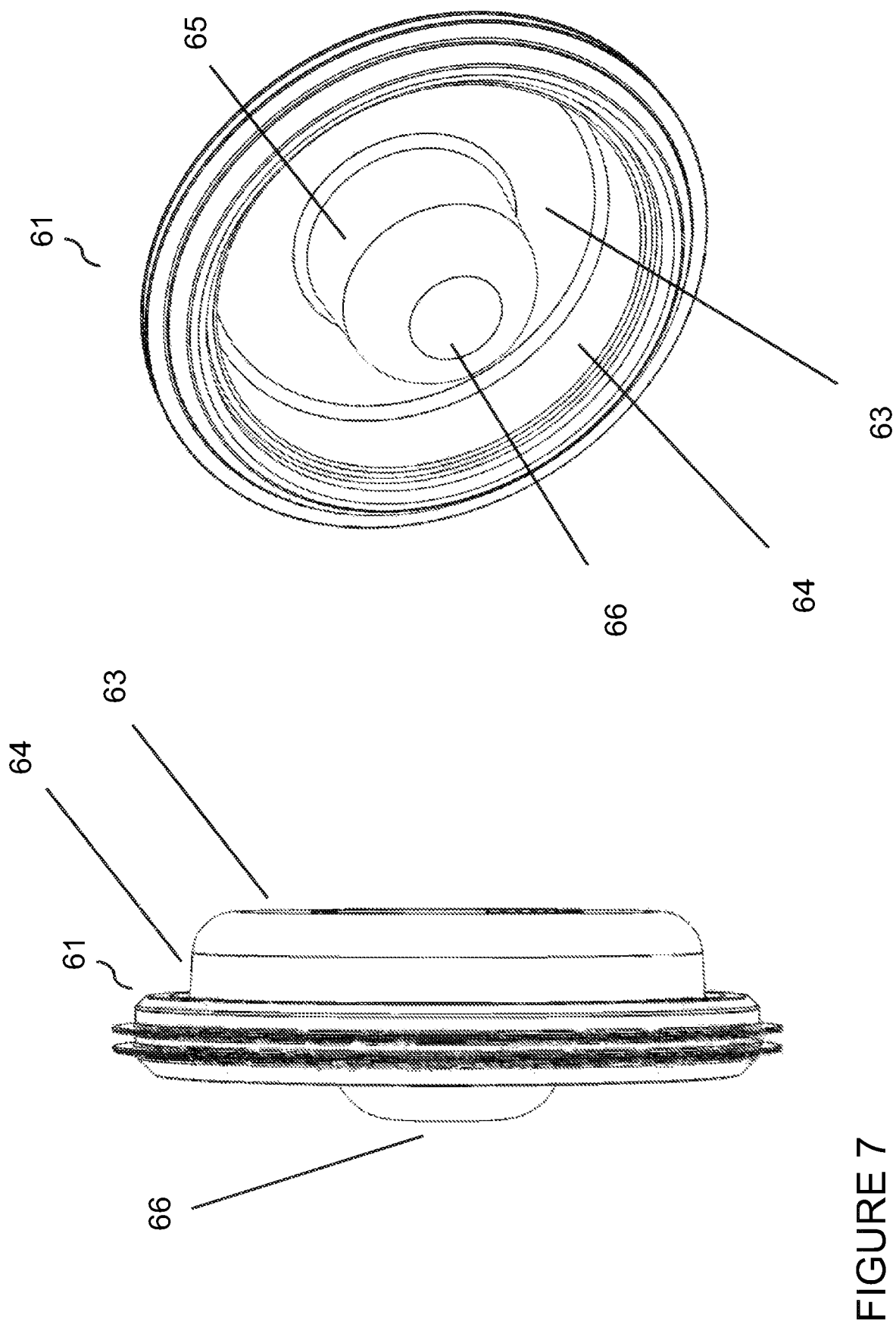
FIG. 7 shows the diaphragm.

FIG. 7 shows the diaphragm 61 in side view and also perspective view. The diaphragm 61 is configured to prevent milk from reaching the pump unit housed inside the control unit 11.

The overall dimensions of the diaphragm are about 77.3 mm in diameter and 24 mm in height (ie depth along the long axis 81 of the nipple tunnel). The volume of air displaced by the diaphragm when under maximum suction is approximately 17550 mm$^3$. Typical variants may have dimensions that are ±25% of these dimensions.

The shape of the diaphragm 61 is not a substantially flat or ridged, convex membrane, as for example found in the Elvie Pump. Instead, it has an outer, approximately cylindrical side wall 64 that is generally parallel to the nipple tunnel 31, and an inner, approximately cylindrical side wall 65 that is also is generally parallel to the nipple tunnel 31. Diaphragm 61 has a front wall 66 that caps the inner side wall 65 and lies over the end of the nipple tunnel 31. It also has an annular rear wall 63 that joins the outer and the inner sides walls 64, 65.

FIG. 8 is a cross section of a breast 85 inserted inside a milk collection hub in a relaxed state, showing the diaphragm 61 in relation to the axis of the nipple tunnel 81, milk port 41 and the pressure chamber 82. The flexible diaphragm 61 includes outer side wall 64 and inner side wall 65, which each substantially run parallel to the center axis of the nipple tunnel 81, and some portions, which substantially run perpendicular to the center axis of the nipple tunnel 81. As illustrated, the diaphragm 61 includes inner annular wall 63 and end cap wall 66 which are perpendicular to the centre axis 81. Much of the flexible diaphragm 61 lies over milk port 41 and also to the right (i.e. away from the breast) of the milk port 41. Milk collection hub 10 is therefore not designed to be compact in the direction of the axis of the nipple tunnel 81. Further, inside the nipple tunnel, the entire volume or space to the right of the nipple and breast is subject to negative pressure; the negative pressure zone hence starts at the skin/air boundary and so flexible diaphragm 61 is entirely to the right (i.e. away from the breast) of the negative pressure zone that is adjacent to the breast. Again, this leads to milk collection hub 10 not being compact in the direction of the axis of the nipple tunnel 81. But that compromise is necessary in order to give the user a clear view down through the clear material of the breast shield 21 nipple and outer shell 20 so that the nipple can be correctly positioned within nipple tunnel 31: correct positioning is very important for comfort and also effective milk expression.

Figure 9:
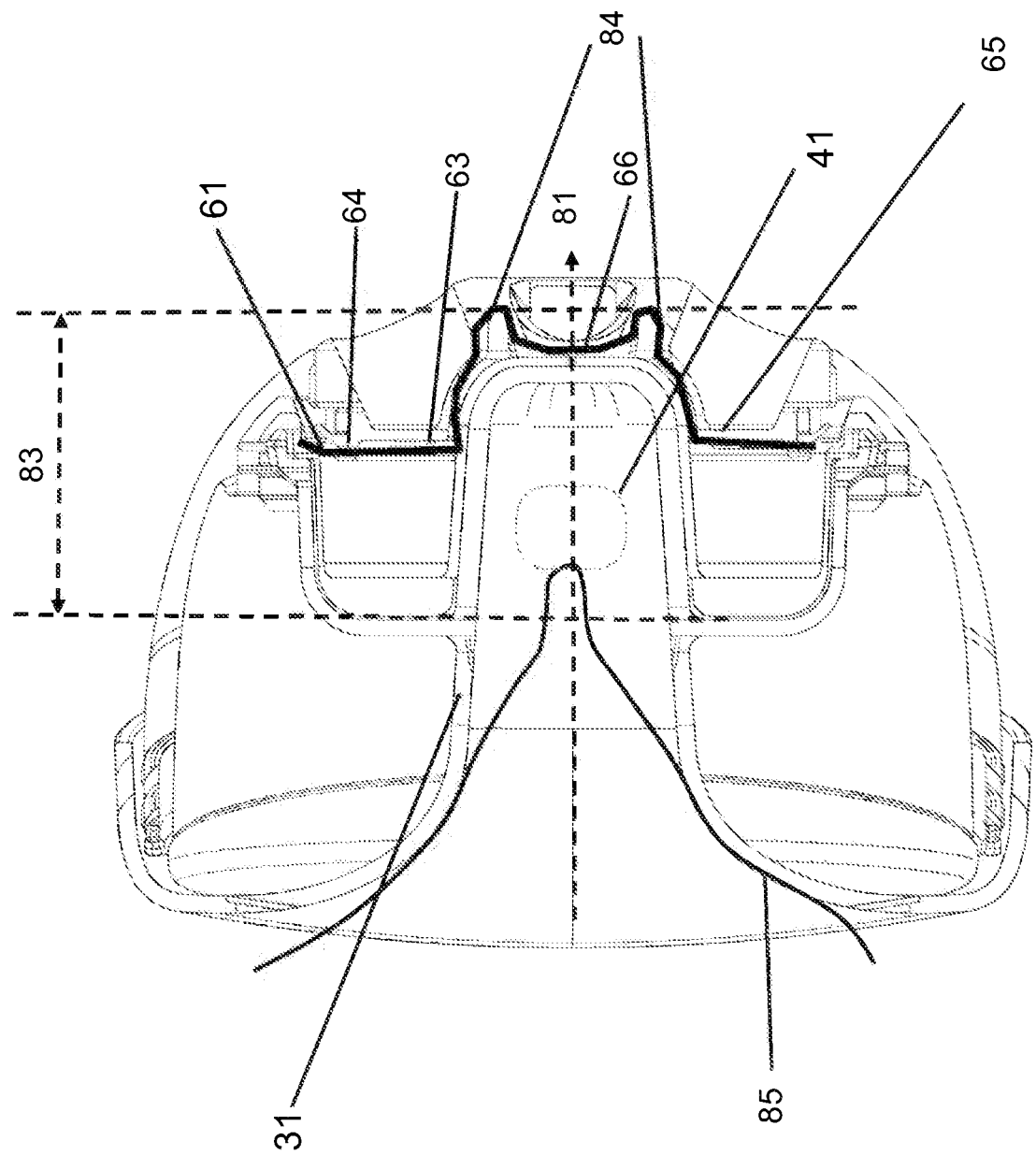
FIG. 9 shows a cross section of a milk collection hub showing the diaphragm under maximum negative pressure.

FIG. 9 is a cross section of the breast 85 inserted inside a milk collection hub showing the diaphragm 61 under maximum negative pressure. During a negative air pressure phase the flexible diaphragm 61 flexes and moves towards the right; even the rear wall 63 moves past the milk port 41. The central section 66 of the diaphragm 61 is at all times located substantially to the right of (i.e. extending beyond) the end of the nipple tunnel 31. During suction, the central section 66 also moves forward into a pair of chambers 84 in the diaphragm cap 22; this additional movement of the diaphragm 61 contributes significantly to the suction achieved inside the nipple tunnel, and hence the milk pumping efficacy.

The diaphragm 61 and associated diaphragm cap 22 are also positioned at the front of the hub 10 so as not to obstruct the mother's view of the nipple when placing the collection hub 10 onto her breast.

Figure 10:
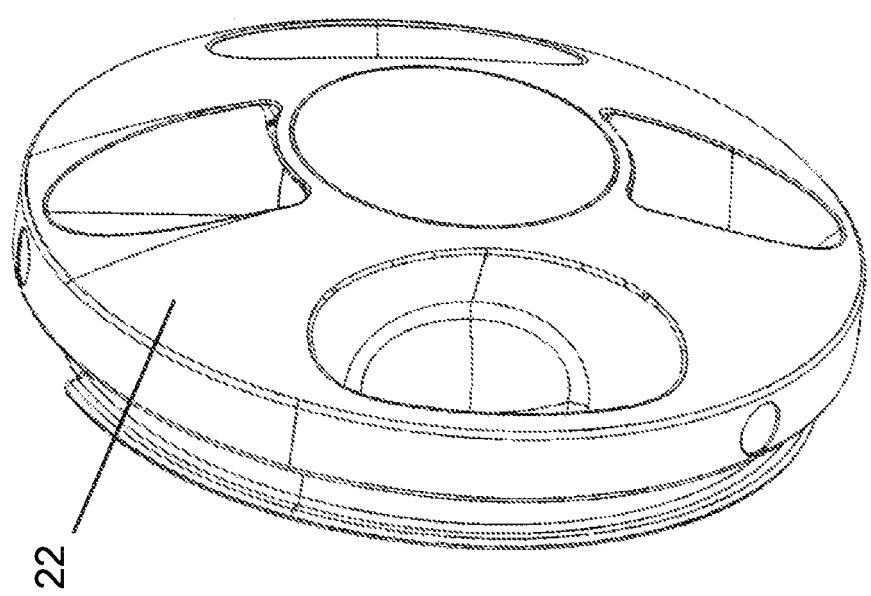
FIG. 10 shows a perspective view of the removable diaphragm cap without the air tube.
Figure 10:
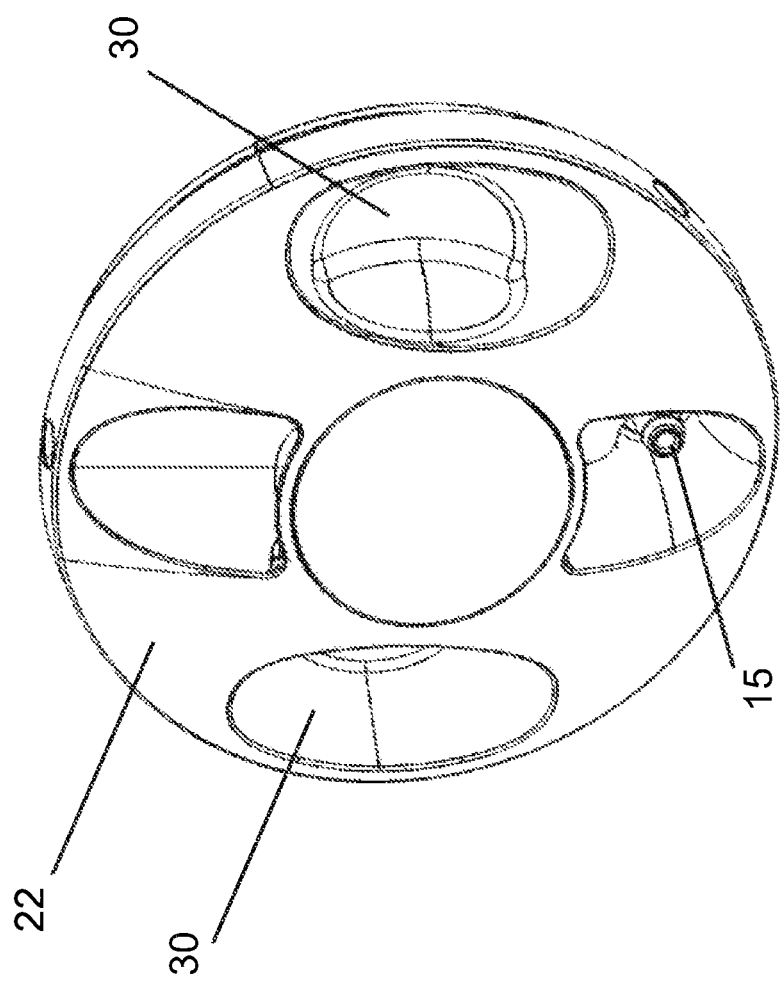

FIG. 10 shows perspective views of the removable diaphragm cap 22. The diaphragm cap 22 includes a pair of hollow or recessed finger grip features 30, making it easily handled using only two fingers. The diaphragm cap 22 is easily rotated so as to adjust the position of the air port 15 and hence the position of air tube 1, 2 (not shown) that would be connected to the air port 15.

Figure 11:
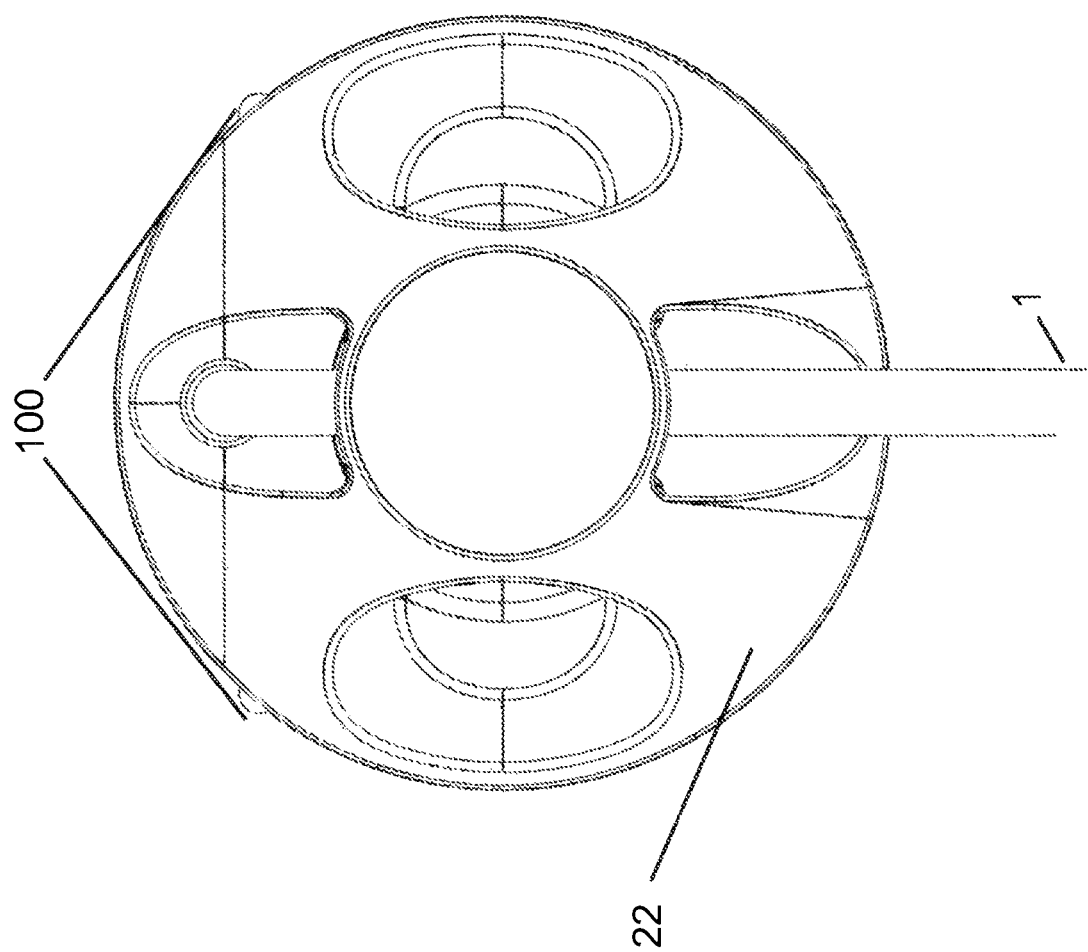
FIG. 11 shows a front view of the removable diaphragm cap connected to the air tube.

FIG. 11 shows a front view of the removable diaphragm cap 22 connected to an air tube 1. The air tube 1 may pass through a passage way located at the center of the diaphragm cap 22, providing an additional protection for the air tube 1 so that it is not, in use, easily pulled out, and so that the direction of the tube 1 conforms with the surface of the inner bra. The diaphragm cap 22 may also be configured to attach to the outer shell 20 by means of a latch system. The diaphragm cap 22 may latch into the outside shell when spring plungers, such as ball bearings 100 in the diaphragm cap, locate into small indents in the outer shell 20. An audible and/or haptic feedback may confirm that the removable diaphragm cap 22 and air tube 1 are properly assembled.

Figure 12:
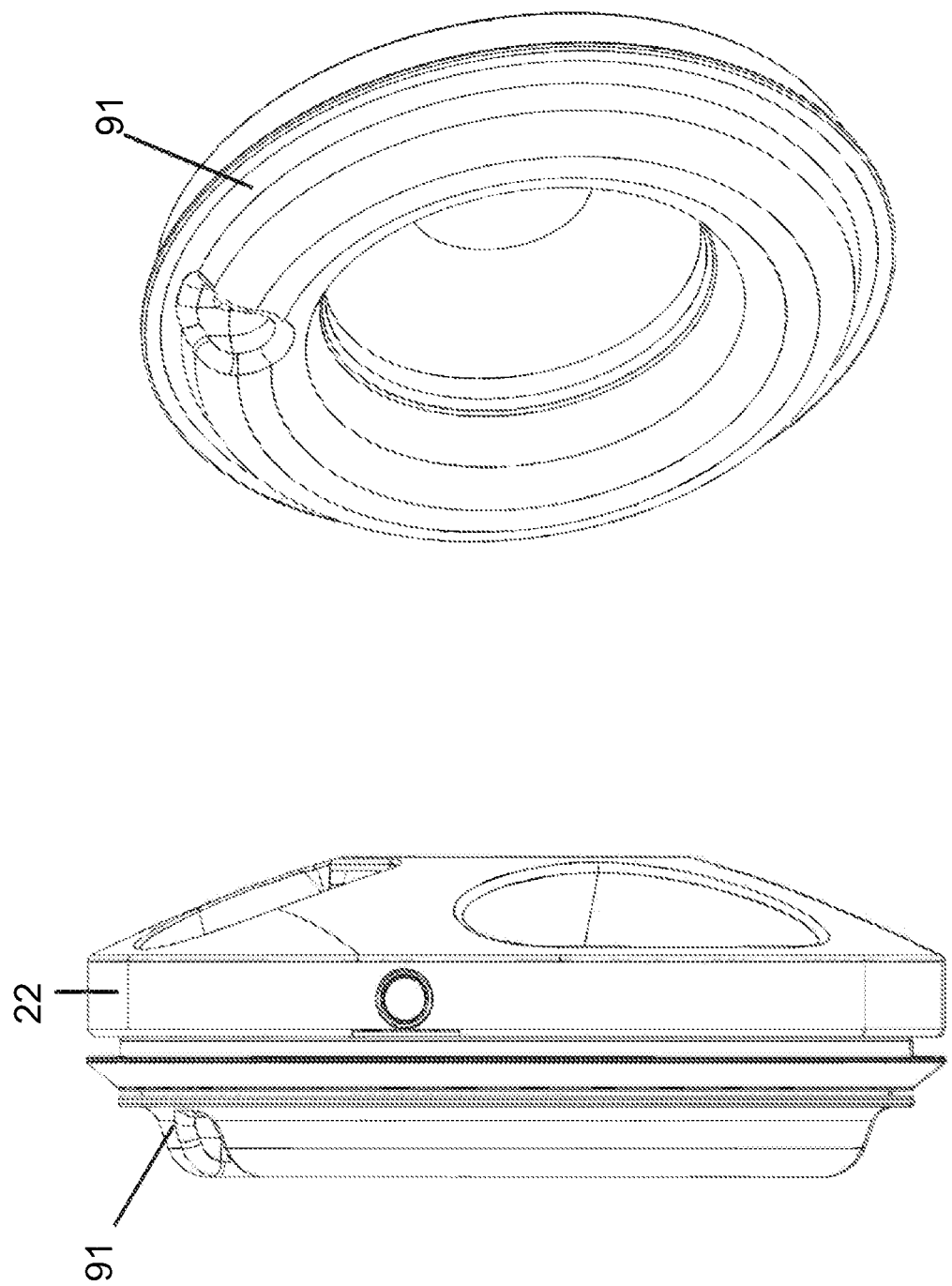
FIG. 12 shows a perspective view of the removable diaphragm cap including the rigid pressure part.

FIG. 12 shows a side view of the removable diaphragm cap 22 including an additional rigid part 91. The additional part 91 is removable from the diaphragm cap 22 and is also shown in isolation. Alternatively, the additional part 91 may be an integral part of the diaphragm cap 22. Additional part 91 reduces the volume of the pump chamber and hence leads to an improved pumping efficiency.

Figure 13A:
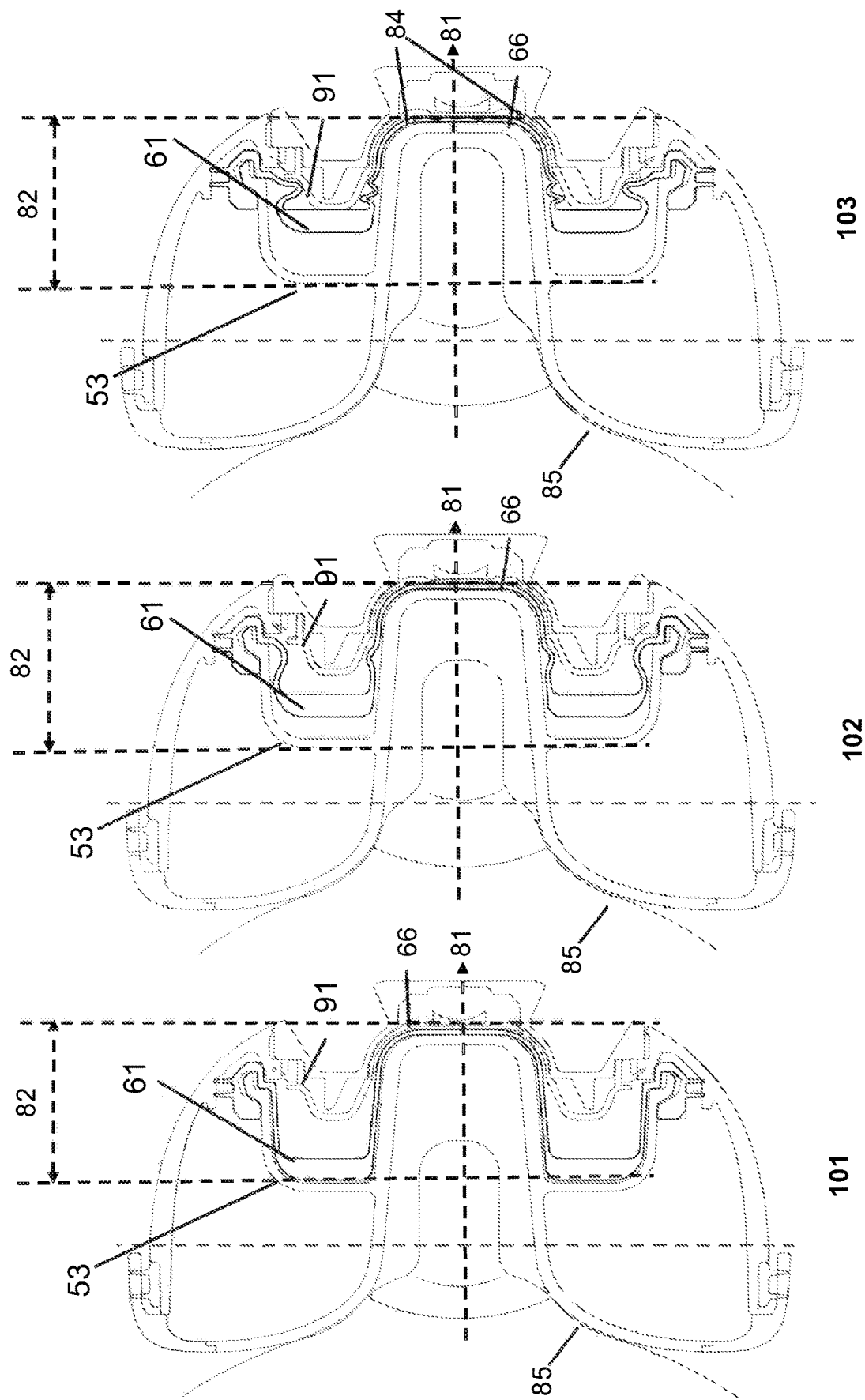
FIG. 13A shows other cross section views of a milk collection hub in a relaxed state, at mid point and under maximum negative pressure.
Figure 13B:
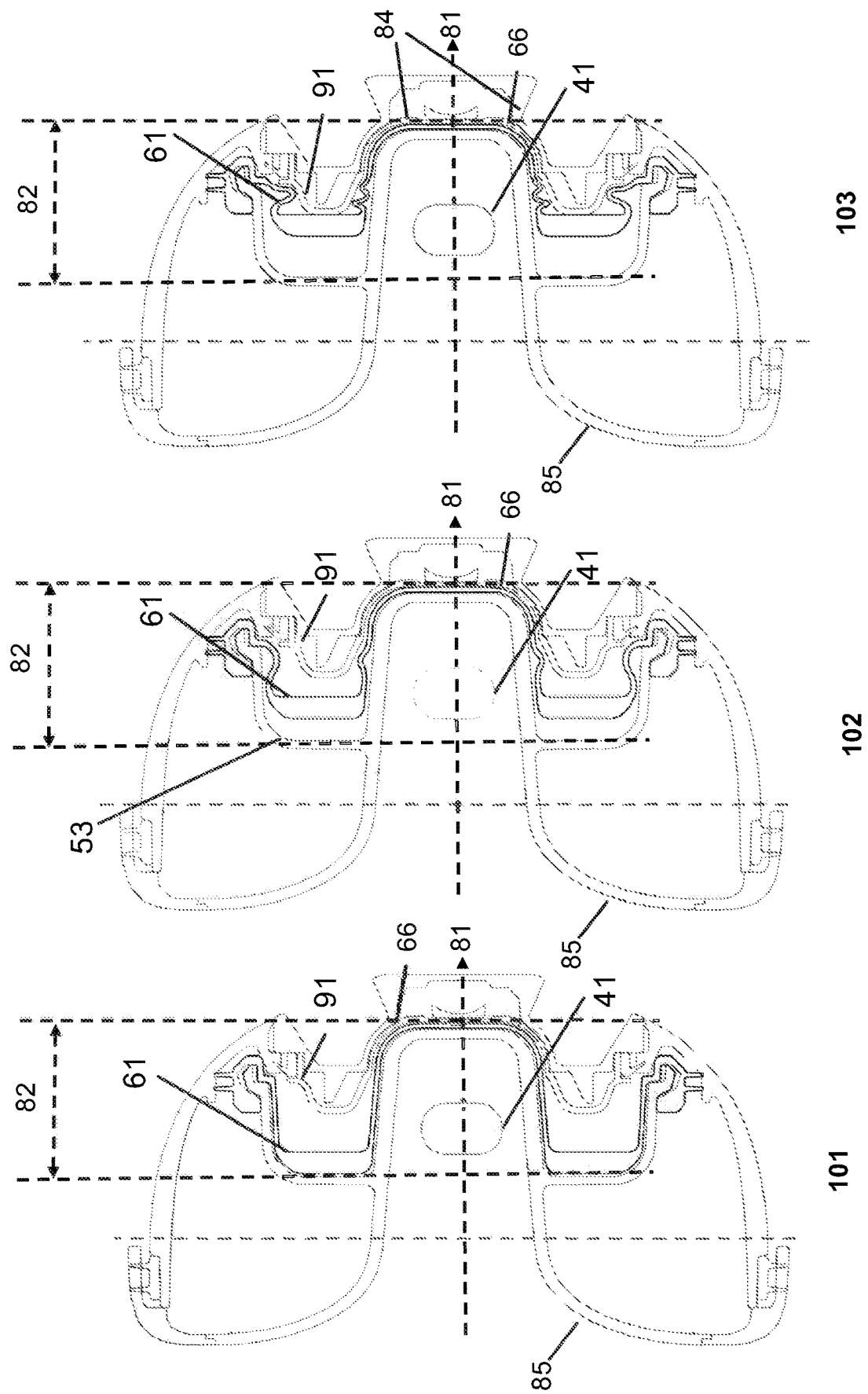
FIG. 13B shows other cross section views of a milk collection hub including the milk port in a relaxed state, at mid point and under maximum negative pressure.

FIG. 13A shows cross sections of a breast 85 inserted in the milk collection hub 10 including the additional rigid part 91 located in the pressure chamber. FIG. 13B shows similar cross sections of the milk collection hub, but without the nipple. Note that the nipple sizing is approximate and that there are considerable variations in nipple size and in how nipples extend when under suction. Note also that these device cross sections are just one example and commercially available devices may differ. Diaphragm 61 is positioned over the end of nipple tunnel 31 and extends beyond the milk port 41 in the direction of axis 81 for the reasons given earlier, namely to provide a clear view of the nipple in the clear nipple tunnel 31. Cross sections illustrate the diaphragm 61 movements from a relaxed state 101, to a mid-point 102 and finally under maximum suction 103. The diaphragm 61 is shown in a relaxed state, in relation to the axis of the nipple tunnel 81, milk port 41 and the pressure chamber. The rigid pressure chamber part 91 reduces the volume of air inside the pressure chamber by limiting the movement of the diaphragm 61 under negative pressure, for example by blocking the pair of chambers 84 in the diaphragm cap 22. The central section 66 of the diaphragm 61 is at all times located substantially to the right of (i.e. extending beyond) the end of the nipple tunnel 31. When suction is applied, the member 61 moves forward along the direction of the central axis 81 of the wearable hub through the negative pressure chamber, as shown in the mid-point illustration 102. The diaphragm 61 becomes flush with the rear surface of the rigid pressure chamber part 91 when it is fully displaced under maximum negative pressure.

In this configuration, by minimizing the volume of air in the pressure chamber, a faster response time and faster cycle time is achieved for single and double pumping, as well as greater peak negative pressure. In one implementation, using single pumping, the minimum pressure is 50 mmHg at cycle time of 75 cycles/min, and the maximum pressure is 350 mmHg at cycle time 30 cycles/min. Using double pumping, the minimum pressure is 30 mmHg at cycle time of 75 cycles/min and the maximum pressure is 280 mmHg at cycle time 30 cycles/min.

Figure 14:
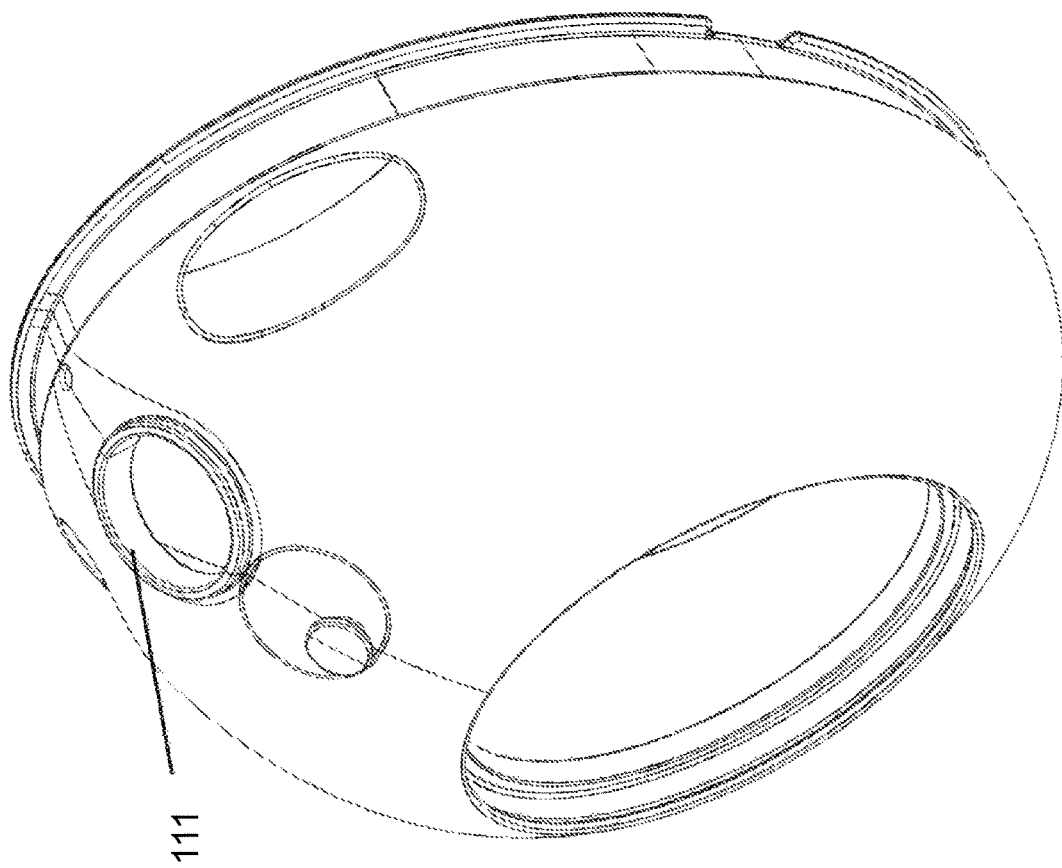
FIG. 14 shows a perspective view of the outer shell, without the removable diaphragm cap.

FIG. 14 shows a perspective view of the outer shell 20 including the milk pouring opening 111.

Figure 15:
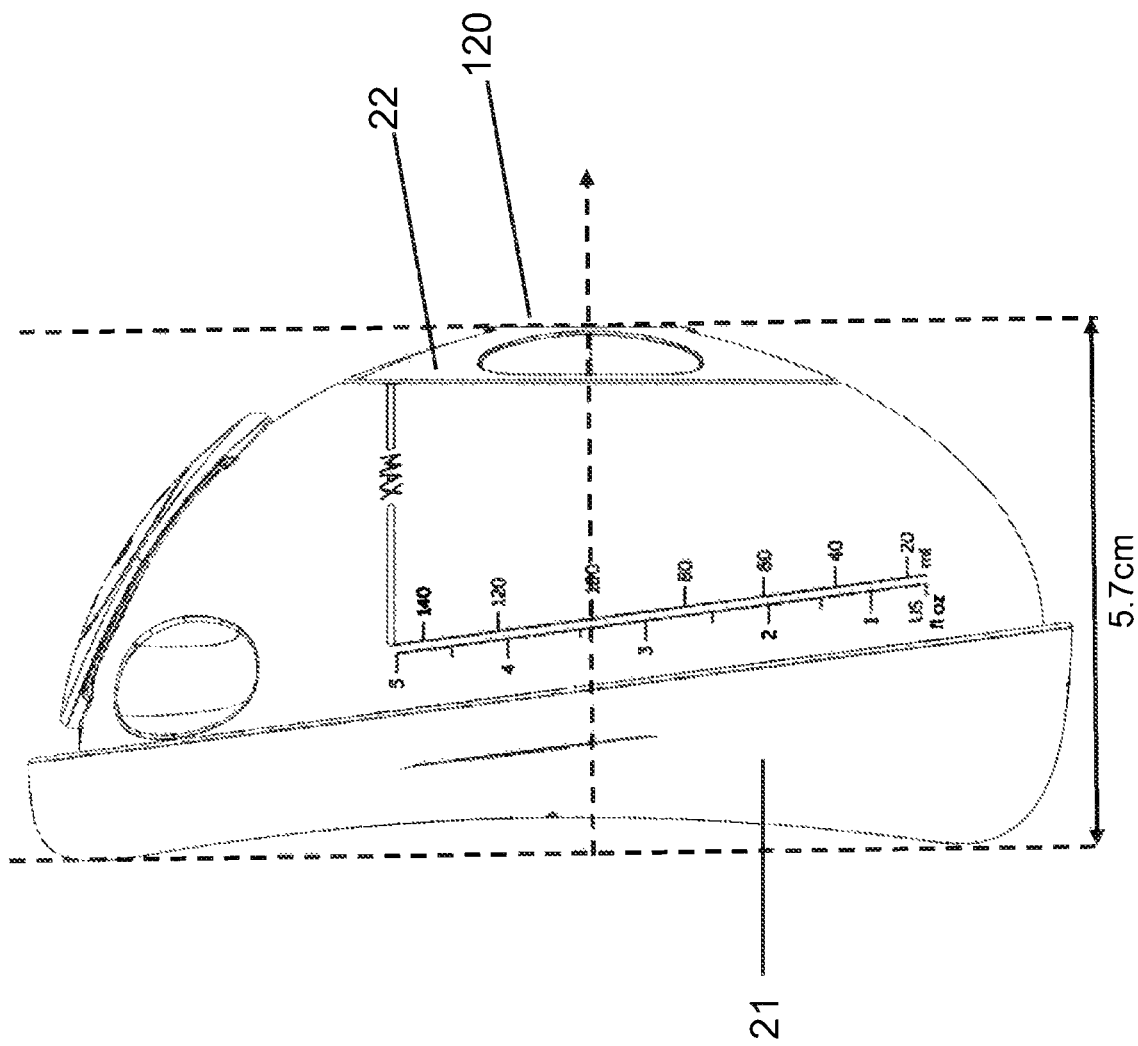
FIG. 15 shows a side view of a milk collection hub.

FIG. 15 shows a side view of a milk collection hub. The overall width dimension of the milk collection hub 10 along the central axis of the nipple tunnel is about 5.7 cm; it is not designed to be particularly thin or compact in the direction of the axial arrow and has a width dimension that is similar or greater than earlier breast collection hubs, such as the Playtex Embrace™. The milk collection hub 10 includes a flat portion 120 located on the diaphragm cap 22, so that the entire milk collection hub 10 can rest on a flat surface with the breast shield 21 uppermost.

Alternatively, the milk collection hub 10 may also include a flat portion on the base of the outer shell 20 such that the entire milk collection hub 10 can rest on a flat surface with the milk opening 111 uppermost.

Control Unit

The control unit 11 is configured to generate negative air pressure for the breast pump system. The control unit 11 has a discreet form and is shaped to comfortably fit in the palm of the hand and be readily gripped by a single hand.

The control unit 11 is shaped to fit inside a pocket (or even a bra). Preferably, the control unit is less than 120 mm in length, less than 70 mm in width and less than 45 mm in height. Preferably, the control unit is less than 0.2 kg.

A user interface 13, provided on the control unit 11, may include buttons, haptic feedback, sliders, any form of display, lights, or any other componentry necessary to control and indicate the use of the breast pump system. The user interface is configured to be intuitive and easy to use.

Figure 16:
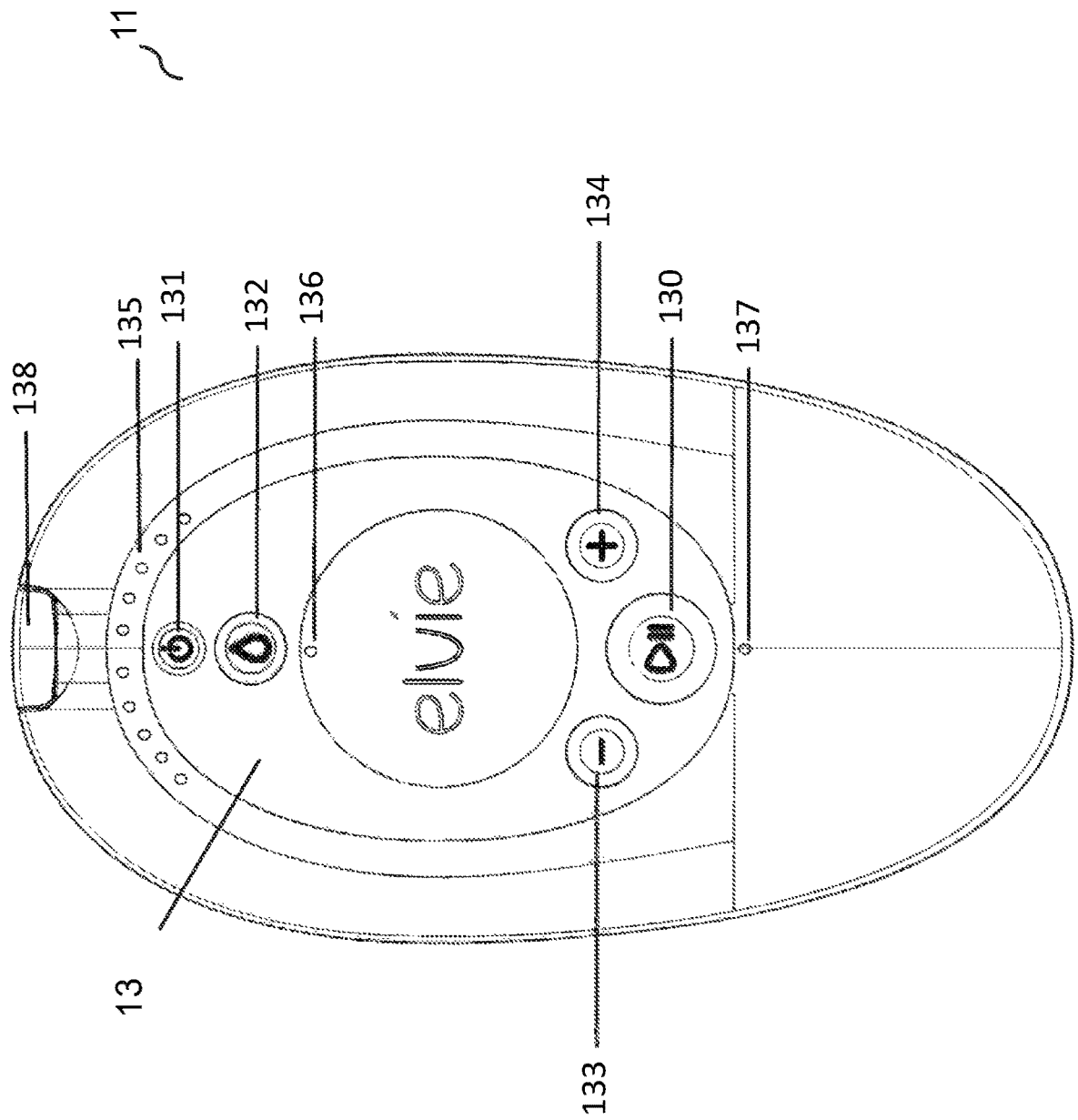
FIG. 16 shows a top down view of the control and air pump unit for the breast pump system.

A particular example of the user interface 13 is provided in FIG. 16 showing the top view of the control unit 11. A power on/off button 131 powers on or off the breast pump system. One button 132 switches the pumping profile, such as between stimulation or expression modes. The buttons 133 and 134 adjust the pressure generated by the pump and hence the vacuum pressure applied to the user's breast(s). A dual function pump/pause button 130 is also provided for the user to interrupt the pumping process without turning the device off.

A visual indicator includes a series of LEDs 135 that change appearance, with more LEDs being illuminated, as the pressure generated by the pump increases. Another visual indicator includes an LED 136 that changes appearance when the pumping profile changes. For example, one color indicates stimulation and another color indicates expression. As another example, the LED is turned off to indicate stimulation and is on to indicate expression. Another visual indicator includes an LED 137 that indicates the battery status. For example, the color red indicates low battery; orange indicates that the battery is charging; while green indicates when the battery is fully charged.

The battery is a rechargeable battery which can be charged via USB. Hence the control unit includes a USB charging socket 138 for transferring power to a power charging circuit housed inside the control unit.

The information provided through the user interface may also be supplemented by or alternatively conveyed solely through haptic feedback. The user interface may also take the form of a touchscreen.

Figure 17:
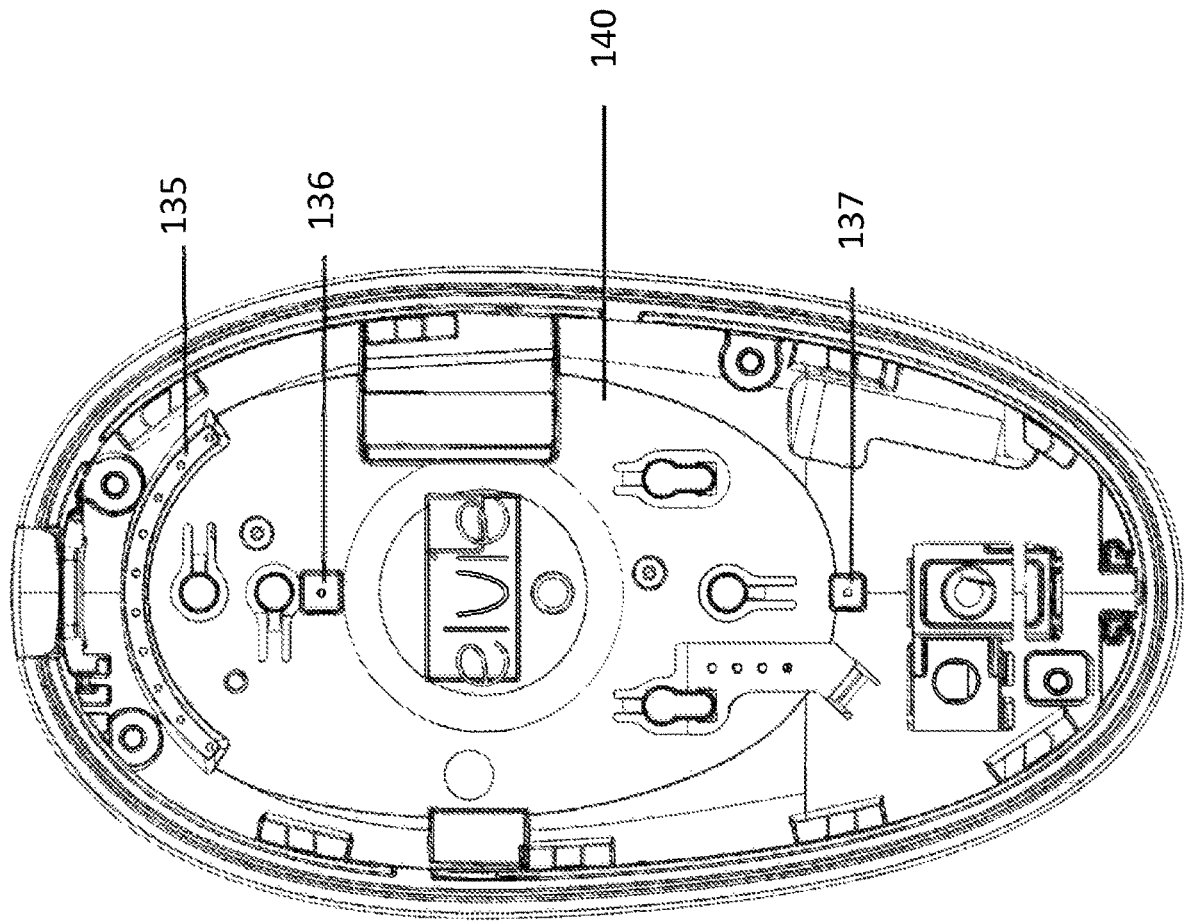
FIG. 17 shows a top down view of the control and air pump unit, with the upper case of the unit removed.

FIG. 17 shows the control unit with the upper case removed. The visual indicators 135 136 and 137 including LEDs are mounted or attached on the chassis 140.

Figure 18:
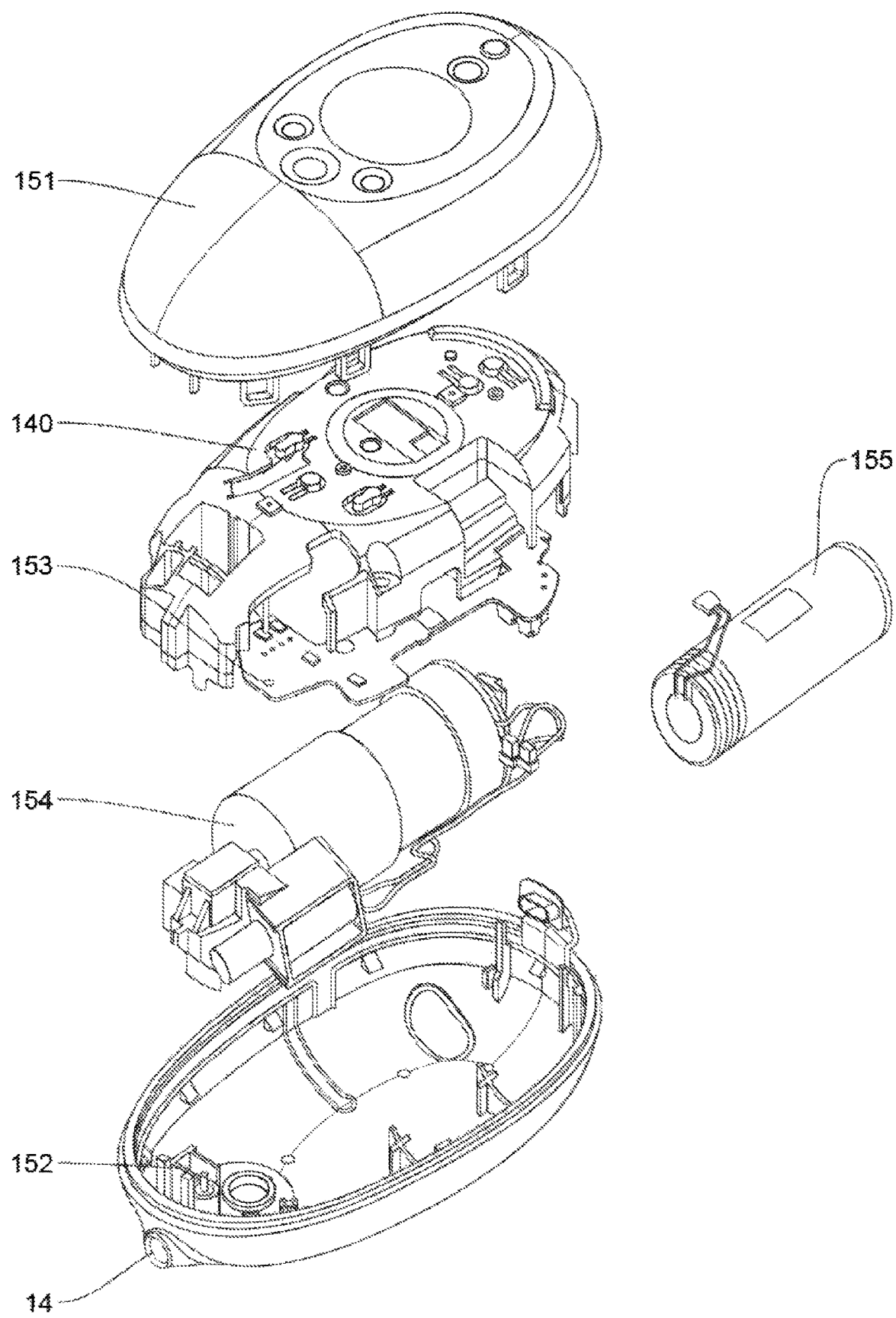
FIG. 18 shows an exploded view of the control and air pump unit.

FIG. 18 shows an exploded view of the control unit U with some of the key internal elements. The outside surface of the control unit is made of an upper case 151 and a lower case 152, which when assembled together are adapted to house, hold and protect the internal components of the control unit 11.

The control unit 11 houses an air pump unit subsystem 154 for generating a negative pressure in the milk collection hub(s), as well as a battery 155 and control electronics on PCB 153. The chassis 140 holds in place the main components such as the air pump unit 154, the battery 155 and the PCB 153. The chassis also includes the actuators between the user interface and the PCB switches.

The breast pump system has been configured to deliver quiet operation in normal use. In particular, the control unit has been configured to both reduce motor vibration and attenuate sound from the pump unit subsystem 154.

Figure 19:
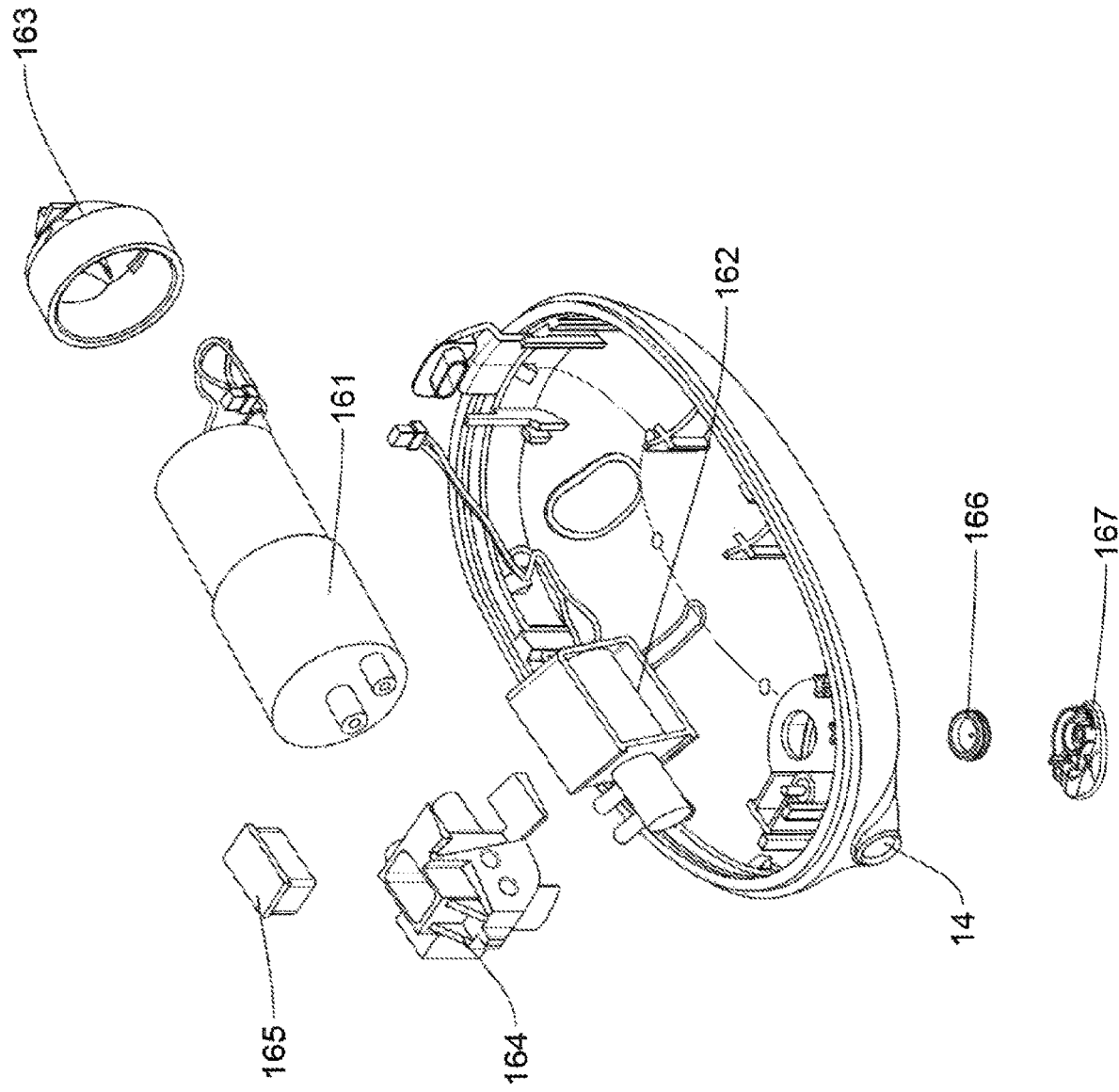
FIG. 19 shows the components of the pump unit subsystem.

The components of the pump unit subsystem 154 are shown in FIG. 19. A pump unit 161, including a pump driven from a motor, is configured to generate negative air pressure. The pump unit 161 is connected to a bleed valve, such as a solenoid valve 162 that is configured to reset the system to ambient pressure when the motor stops.

Reduction of Motor Vibration and Attenuation of Sound

The breast pump system is designed to be more discreet compared to available solutions with respect to volume and sharpness of noise. This is enabled by one or more of the following: reducing the sound generated by the pump unit 161; soundproofing the control unit 11; reducing the power of the pump unit 161, reducing the bleed sound by slowing down the airflow speed during rapid return to ambient air pressure after each pumping cycle, and absorbing the vibration of the pump motor in the pump unit subsystem 154.

The motor vibrations are reduced by holding the pump unit 161 in place between two silicone parts: a sound attenuating motor mount 163 and an airflow block 164. The sound attenuating motor mount 163 holds the back of the pump motor and absorbs part of the vibration of the pump motor. The airflow block 164 includes an air port or hole for routing the airflow from the pump unit 161 to the tube connector 14 and also absorbs part of the vibration of the pump unit. By using the two silicone parts, the vibration transmitted to the hard plastic case 151, 152 is greatly reduced and hence the unit is significantly quieter than other pumping units; a major advantage when discretion is sought, and to reduce disturbance to baby.

Both the sound attenuating motor mount 163 and the airflow block 164 are one-piece items made of either compression-moulded or ISR moulded silicone.

Figure 20:
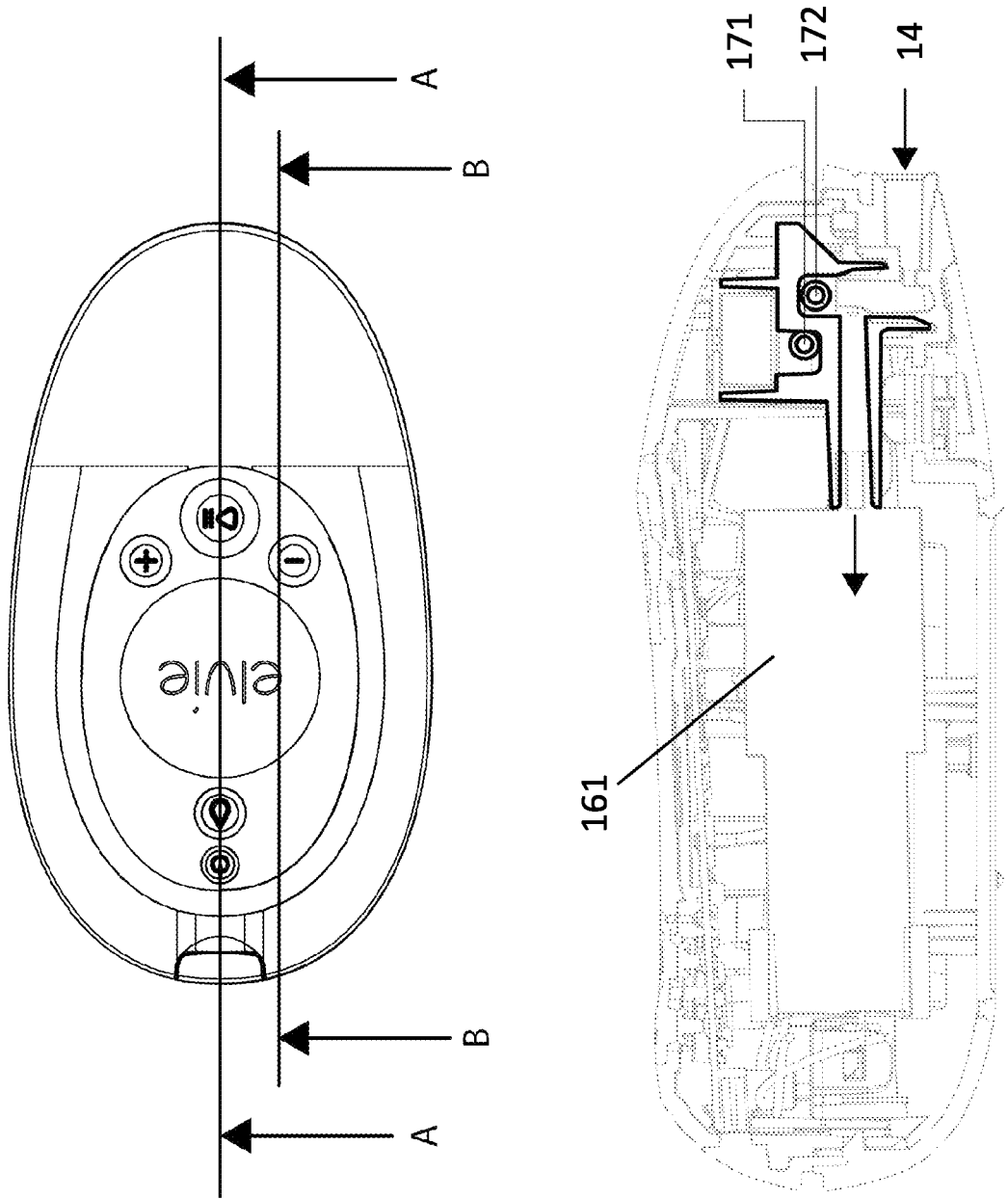
FIG. 20 shows a cross section of the airflow block inside the control unit.
Figure 21:
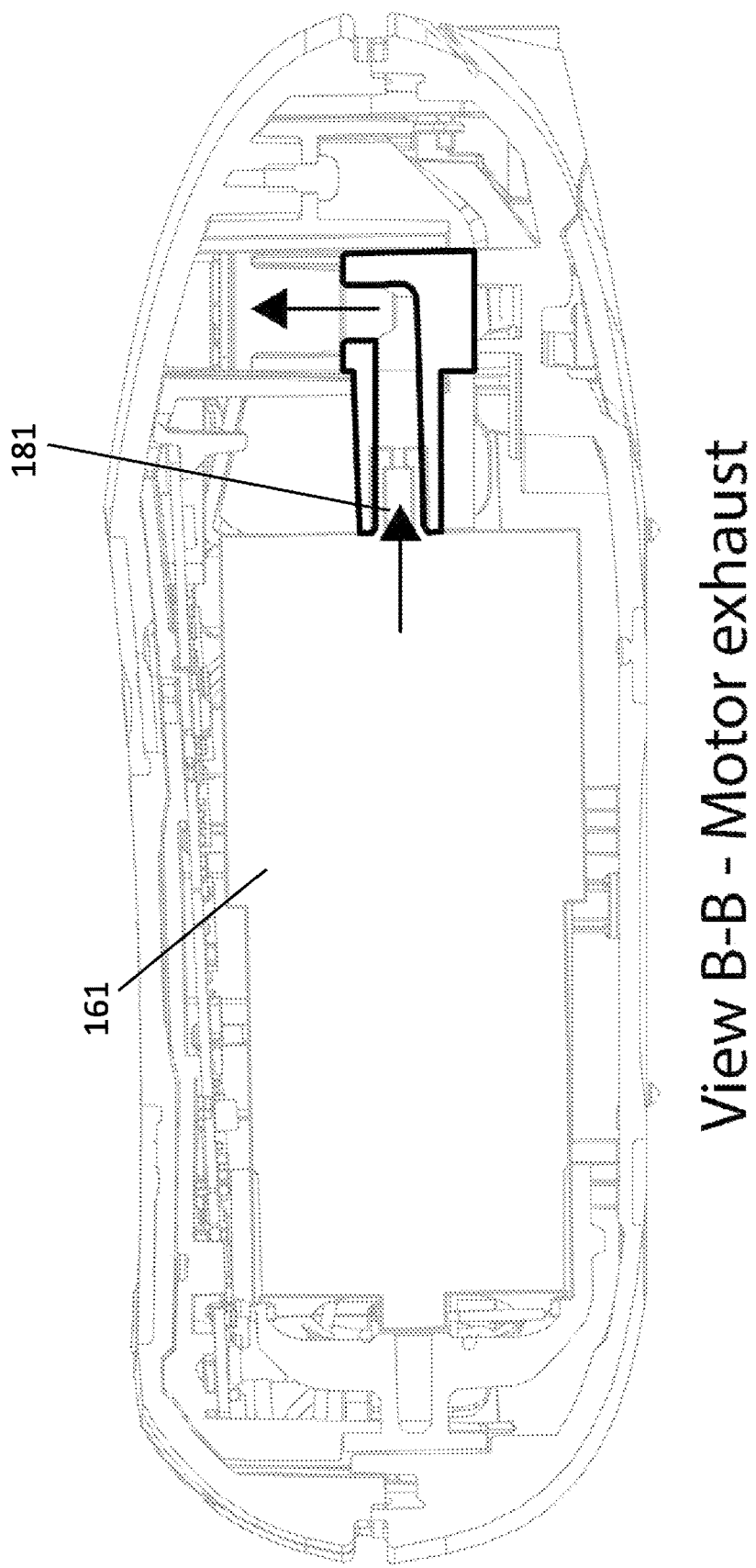
FIG. 21 shows a cross section of the airflow block inside the control unit.
Figure 22:
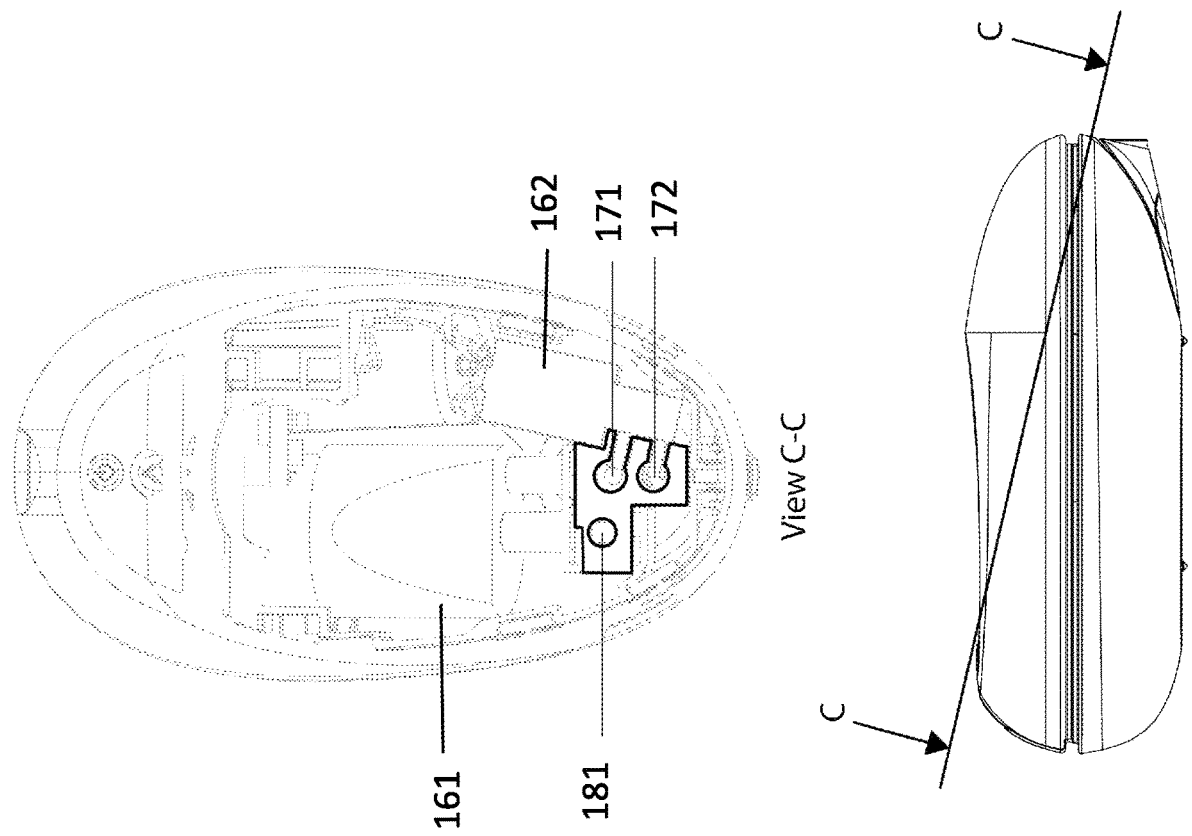
FIG. 22 shows a cross section of the airflow block inside the control unit.

FIGS. 20 to 22 provide cross sections of the airflow block that illustrates the air paths inside the airflow block. The airflow block 164 is a multifunctional block that:
  routes or directs the airflow from the tube connector 14 or inlet to the pump unit 161 (see FIG. 20).
  directs the air from the motor exhaust 181 to the atmosphere through a simple straight hollow tube with an exit path at one end (see FIG. 21).
  provides the mounting for the solenoid valve inlet 171 and outlet 172 (see FIGS. 20 and 22).
  provides an isolation barrier for motor vibrations.

The airflow block 164 therefore is configured to both attenuate sound and to reduce motor vibration.

A number of components may be used to further reduce the sound generated by the pump unit subsystem including, but not limited to:
  A solenoid foam cap 165 to reduce bleed flow as well as bleed sound.
  A sound valve 166 (as shown also in FIG. 23) located in the lower portion of the case 152. The sound valve 166 allows the internal pressure of the control unit 11 to remain at ambient pressure without high levels of sound escaping from the control unit 11. A sound valve cap 167 is also used to protect the sound valve 166 from the external environment.
  Sealing the control unit 11 so as to further attenuate sound. For example, a seal member 173 (see FIG. 23) is included in between the upper part 151 and lower part 152 of the case, around the periphery of the control unit 11, hence allowing no air to escape from the control unit 11, to reduce the pump unit 161 sounds from travelling outside the control unit 11. Optionally, the airflow block 164 may also be integrated with a portion of the seal member 173.
  Mufflers or silencers can also be used reduce the airborne noise emitted from air inlets and/or exhausts. One silencer can be connected to the solenoid 162 and another silencer can be connected to the pump motor.

Figure 23:
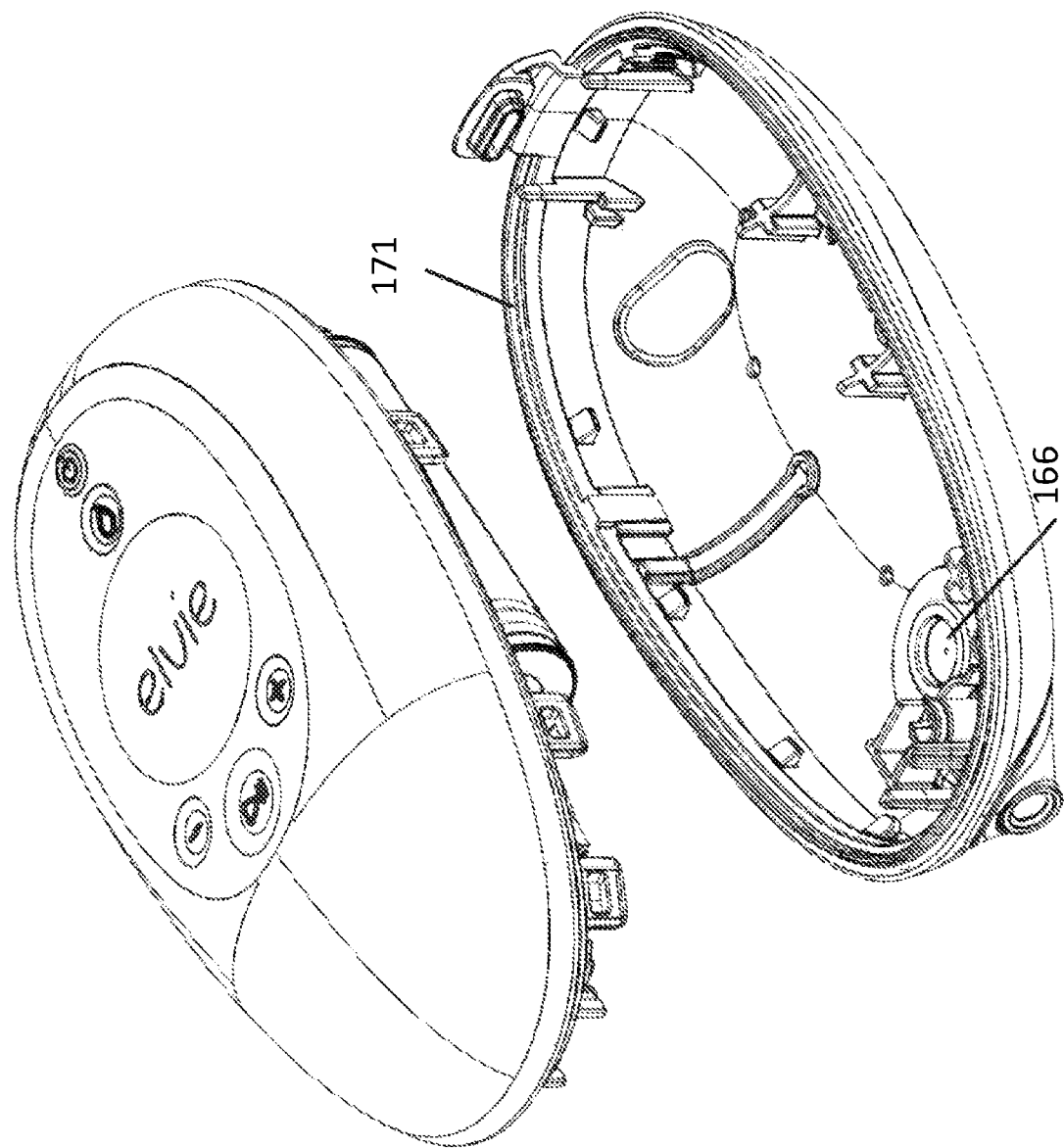
FIG. 23 shows the sound valve.

The sound valve 166 located on the lower part 152 of the case is shown in FIGS. 19 and 23. The sound valve 166 is a silicone part configured to deform under pressure. Hence it allows the air to pass in and out of the control unit 11, whilst significantly attenuating the motor and pump noise from travelling out of the control unit 11. The sound valve 166 also ensures that the inside of the control unit 11 remains at ambient pressure and that the pump unit 161 is working in the right conditions.

The sound valve may include a small cross section cut.

Figure 24:
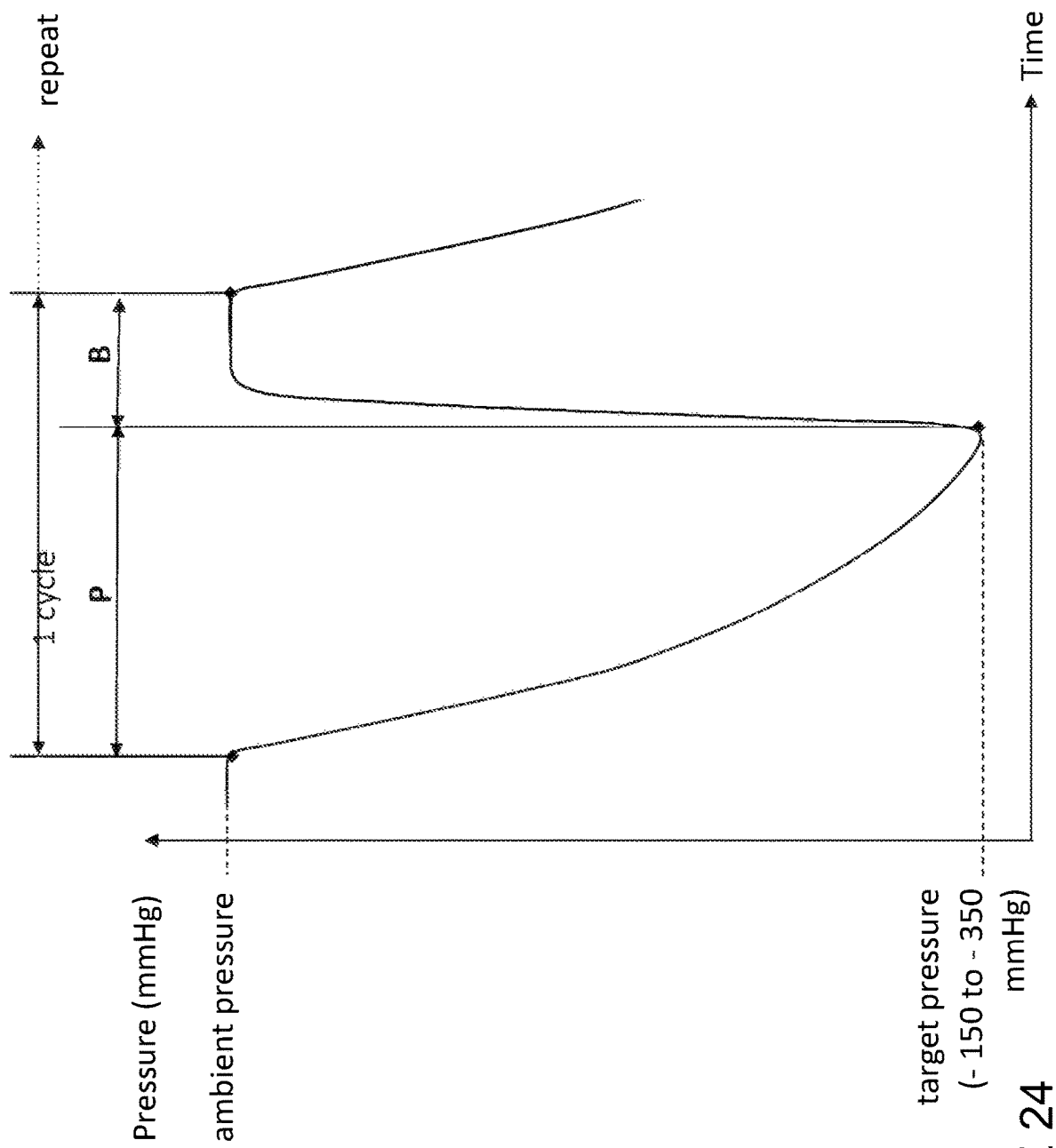
FIG. 24 shows a plot of the pumping cycle.
Figure 25:
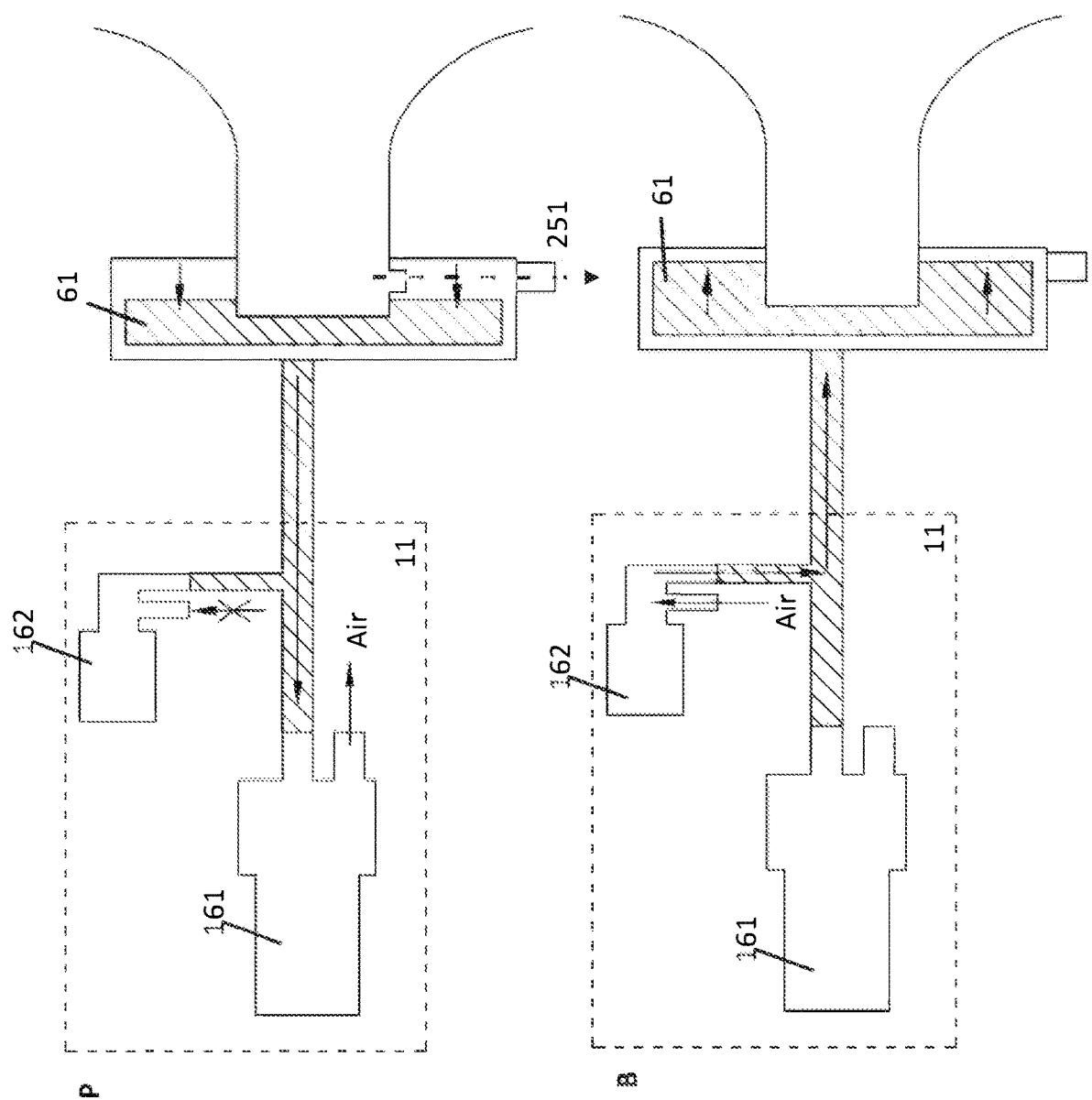
FIG. 25 shows schematics of the pump unit subsystem illustrating the pumping cycle.
Figure 26:
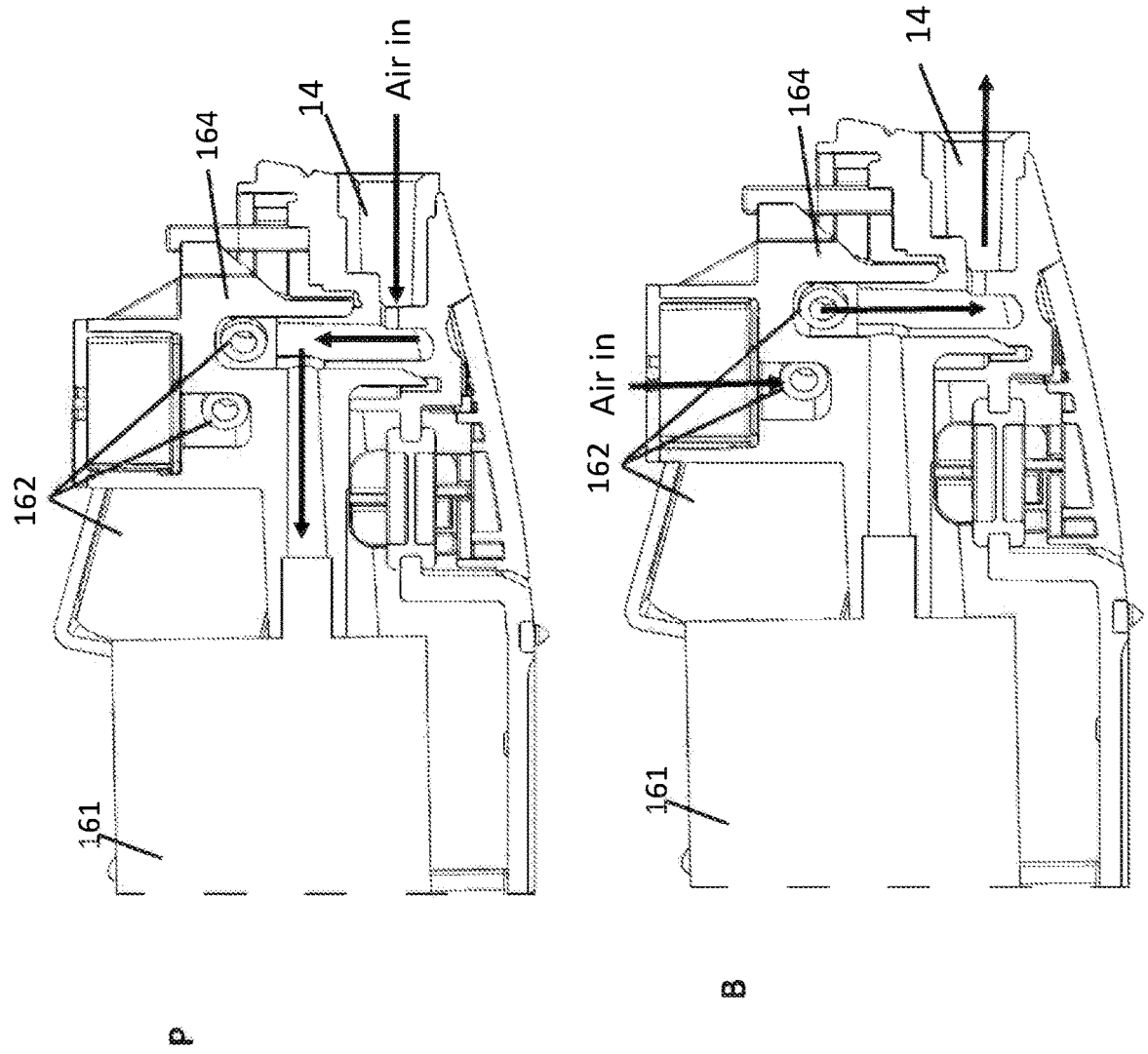
FIG. 26 shows cross-sections of the control unit including the pump unit subsystem illustrating the pumping cycle.

The pumping cycle is now described in FIGS. 24 to 26.

Once the system is activated, a pumping cycle begins: the air-pressure pump turns on and creates negative air pressure during a first phase of the pumping cycle, referred to as the pumping time (P). When negative air pressure is applied to the milk collection hubs 10, the flexible diaphragm 61 flexes and negative air pressure is conveyed to the inside of the nipple tunnel 31, to pull the breast and/or nipple, thus drawing milk 251 from the nipple. During this first phase of the pumping cycle (P), the air-pressure pump 161 is configured to be on for a pre-defined amount of time in order to provide a target negative air pressure. During this first phase, the solenoid valve 162 is configured to be turned off.

After the target negative air pressure has been reached, the air-pressure pump 161 turns off, and air is bled into the system via the solenoid valve 162 during the second phase of the pumping cycle referred to as bleed time (B). At the end of the bleed time, the system is therefore reset to ambient pressure.

Figure 27:
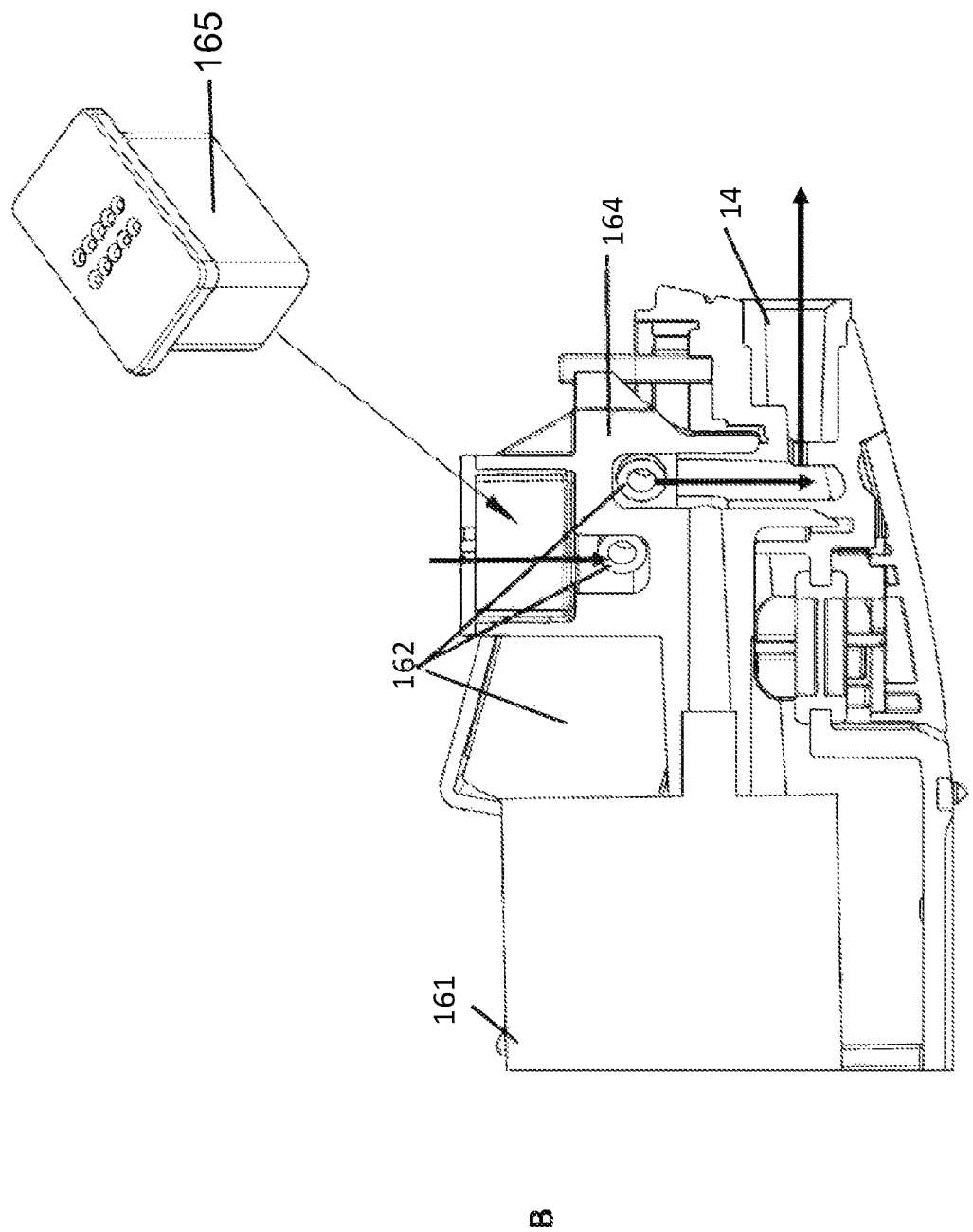
FIG. 27 shows a cross section of the control unit including pump unit subsystem.

During this second phase of the pumping cycle, the solenoid valve 162 opens to reset the pressure in the milk collection hubs 10 to ambient, which causes a rush of air into the solenoid valve 162 and generates a sound, such as a sharp, high frequency sound. As discussed above, using a solenoid foam cap 165, as shown in FIG. 27, reduces the rush of air entering the solenoid valve 162 and therefore reduces the overall sound generated by the solenoid valve 162. The solenoid foam cap 165 includes one or more small openings or holes that are configured to reduce and control air speed when entering the solenoid valve 162. The solenoid foam cap 165 may be a one-piece item made of plastic.

The pumping cycle may be programmed to follow different modes, such as a stimulation mode and an expression mode, by controlling the pumping time and the bleed time. The pumping cycle and/or modes may also be programmed to reach different vacuum levels.

Stimulation mode is configured to encourage milk flow and expression mode is configured to maximize pumping efficiency. Each mode contains a number of different vacuum levels, such as 10 different vacuum levels, which can be selected via the user interface on the control unit.

FIG. 28 lists an example of 10 different vacuum levels for stimulation and expression modes and for single and double pumping. This is one example and commercially available devices may differ. Adjusting the power delivered to the pump motor also reduces the sound generated by the system.

Hence a desired vacuum level and sound for a particular mode may be achieved by controlling the time of both phases of the pumping cycle and the power delivered to the pump motor.

The perimeter of the control unit has a complete seal 173 (see FIG. 23), dramatically reducing the airborne noise leaving the unit. This seal creates a significantly quieter product for the user.

Overall, in operation, the noise level is less than 50 dB and preferably less than 45 dB.

A number of removable accessories may be used that attach to the control unit 11 to improve the user experience. These may include for example:

- a removable, auxiliary battery pack for increasing the length of time a user can pump for between charges.
- a tube wrap device that clips to the back of the control unit, allowing the user to neatly store the tubes by wrapping them. This may also allow the user to customise the length of their tubes during use.
- a belt clip that allows the user to attach the control unit to their clothing, wearing it on their waistline or elsewhere.
- a lanyard that clips to the control unit, allowing the user to wear the control unit by hanging it around their neck.

The attachment method for accessories may involve an O-ring style loop that stretches over the control unit in multiple positions, allowing a control unit to be mounted in either portrait or landscape orientation.

Accessories for the Control Unit

The control unit may also include a number of easily removable accessories.

Figure 29:
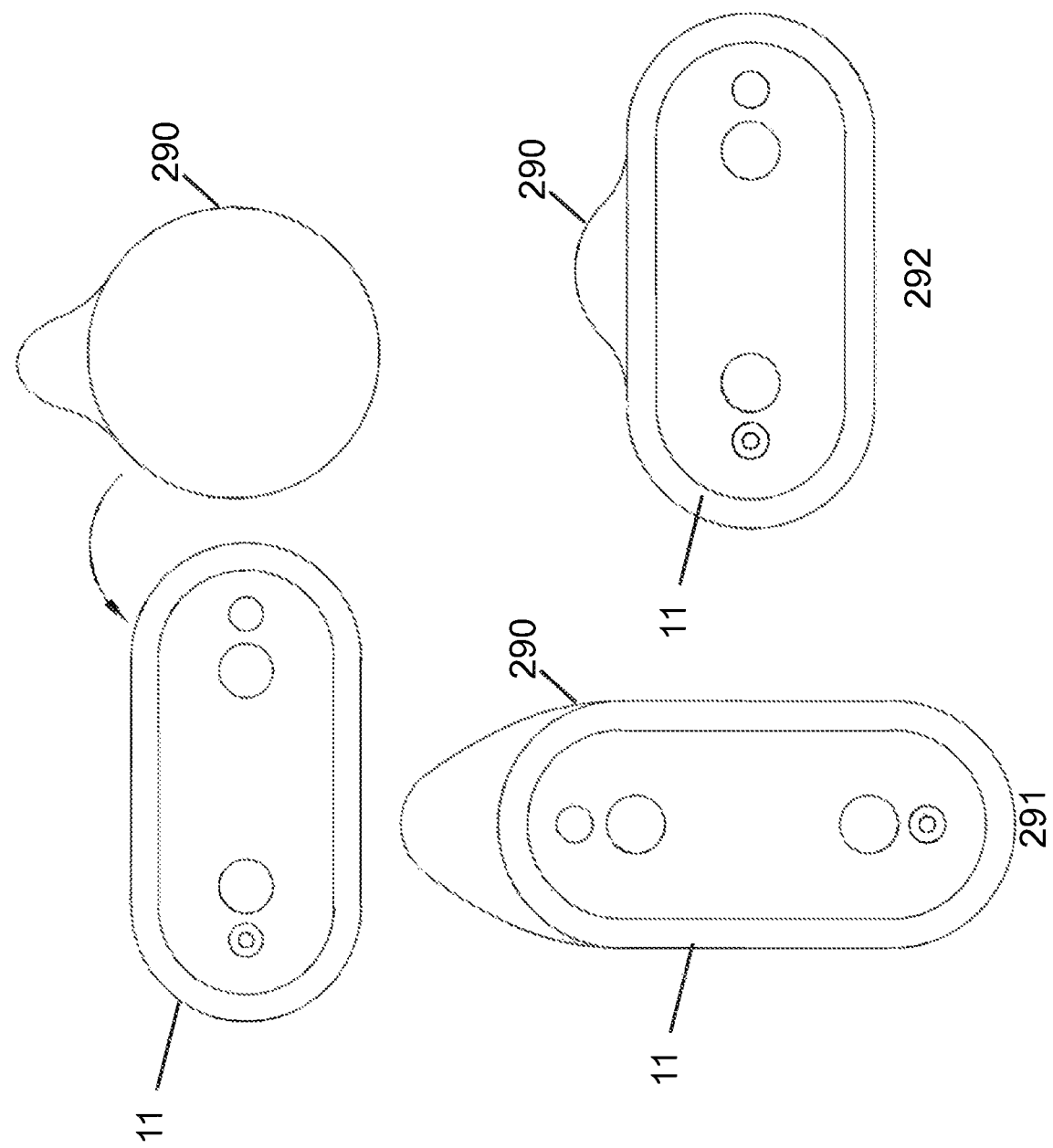
FIG. 29 shows diagrams of a control unit including a multifunction mount.

FIG. 29 shows diagrams of a control unit 11 including a multifunction mount such as an O-ring 290. The multifunction mount enables the control unit 11 to be easily held by the user's fingers in different modes, such as portrait 291 or landscape mode 292.

Figure 30:
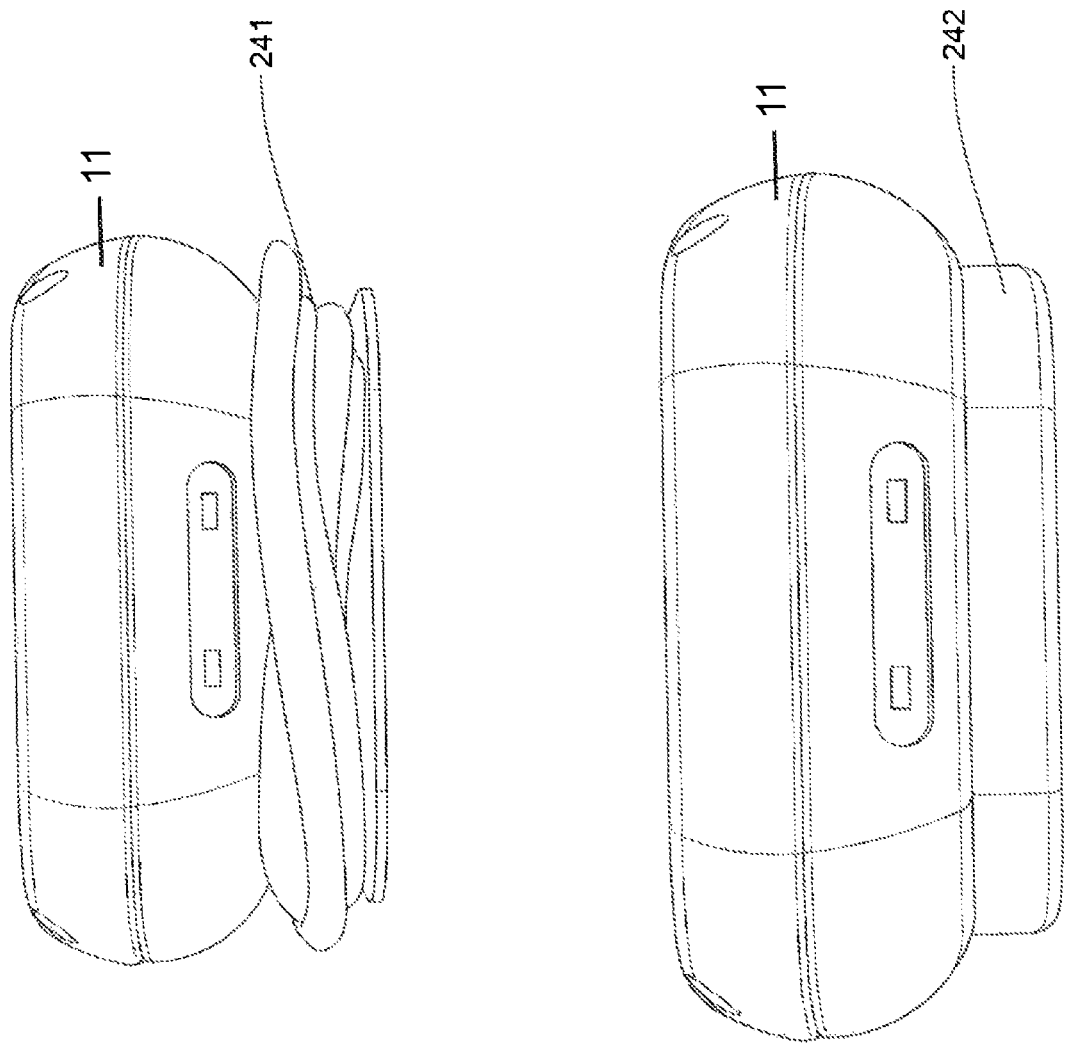
FIG. 30 shows pictures of a control unit including accessories.

FIG. 30 shows pictures of the control unit 11 including a tube wrap accessory 241 located under the bottom case of the control unit 11, and of the control unit including a battery accessory 242 located under the bottom case of the control unit 11, such as a battery pack.

Figure 31:
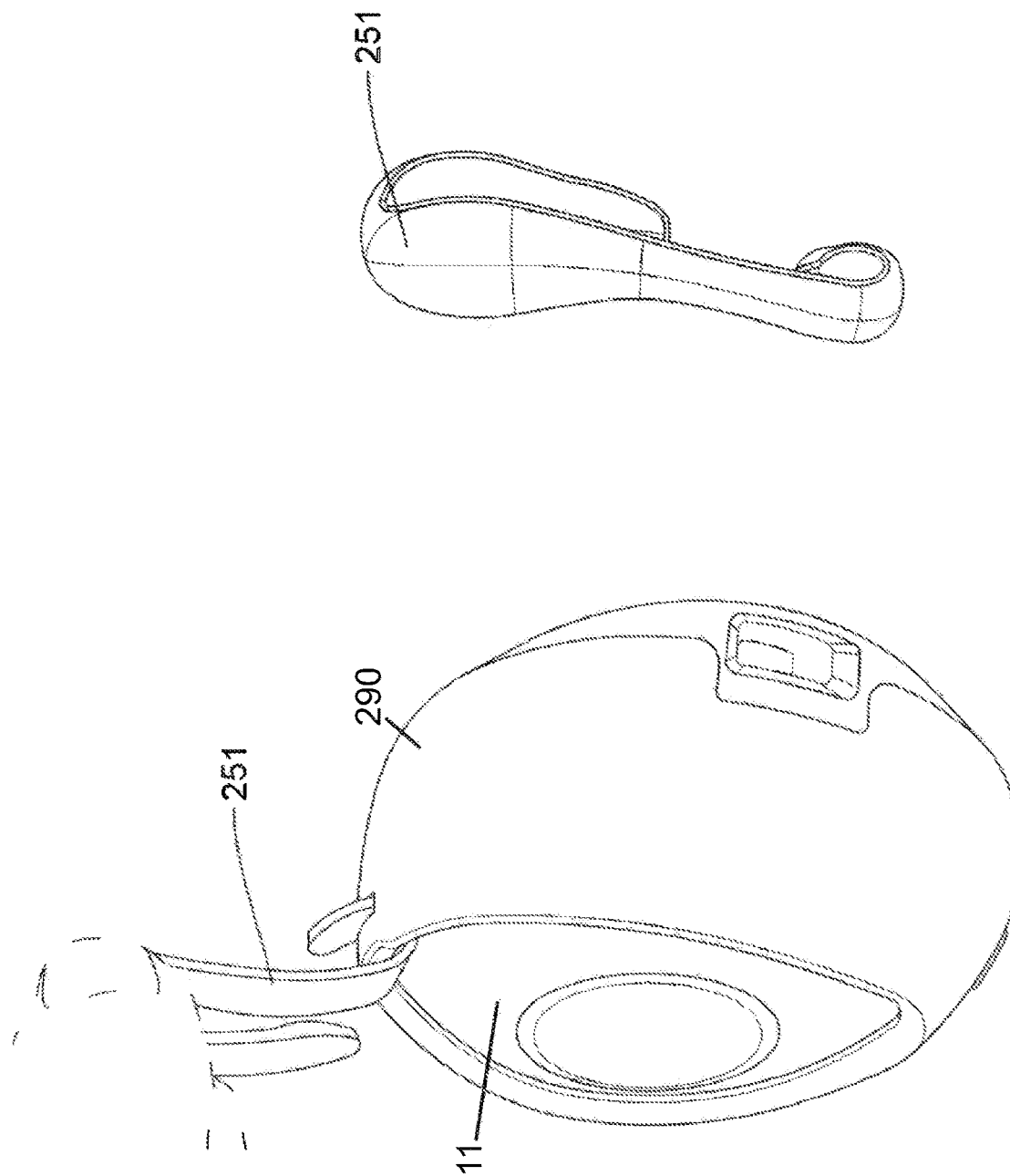
FIG. 31 shows diagrams of a control unit including a multifunction mount.

FIG. 31 shows a picture of a control unit 11 including an o-ring 290 mount extending around a periphery of the control unit 11. The mount including a removable waistband clip 261 enabling the control unit to be, for example, clipped to a belt or trousers.

Tube Connection

Figure 32:
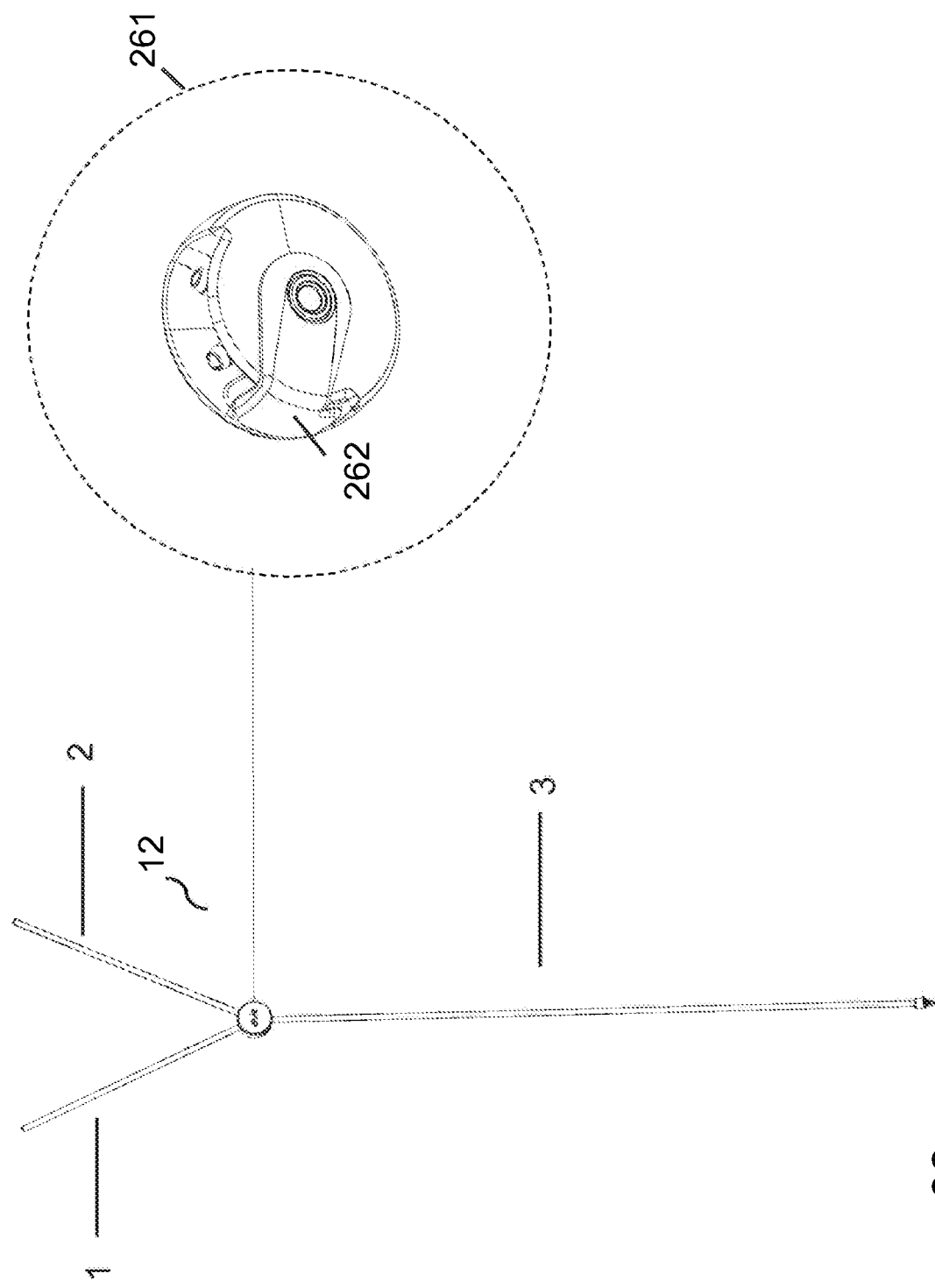
FIG. 32 shows the tube connection.

FIG. 32 shows the tube connection 12 including the tube splitter 261. The tube splitter 12 in effect splits the air line 3 that comes from the combined control and air pump unit 11 into two separate air lines 1, 2 that attach to the two milk collection hubs 10. Tube splitter 12 attaches to one end of the air lines 1, 2 that are connected at their other end to the air port 14 in each milk collection hub 10. The tube splitter attaches to one end of the air line 3 that is connected at its other end to the combined control and air pump unit 11. Tube splitter 12 includes a bung or stopper 262 that can be rotated in order to configure the breast pump system for single pumping or double pumping, by creating an air path that leads from air line 3 into either the left airline 1 or the right air line 2 to activate respectively just the left hub or the right hub; or it can create an air path that leads from air line 3 into both left airline 1 and also right air line 2, for double pumping.

Application Running on a Connected Device

Pump system related data may be sent by the system to a connected smartphone or other computer device. The data may be further analysed by a data analysis subsystem. The data may also be displayed on an application running on the computing device.

The application may provide one or more of the following features:

- Discreet/Remote control of device, such as: play/pause, mode change, intensity setting change.
- Battery life indication.
- Session time and date tracking.
- Milk volume tracking.
- Integration with other devices, such as other breast pump system.

APPENDIX 1

Key features of the breast pump system are now generalized into the following categories:
A. User experience: Nipple Visibility
B. Cost Engineering: Simplicity
C. User Experience: Low Noise
D. User experience: Product Handling Note that any feature can be combined with any one or more other features. The invention is however defined in the appended claims. Note further that, whilst the implementation described above is a breast pump system with one or two in-bra wearable milk collection hubs, each connected to an external air pump, it is possible to integrate an air pumping mechanism, rechargeable battery and control electronics inside each milk collection hub, in much the same way as the Elvie Pump (see WO 2018/229504) integrates an air pump, rechargeable battery and control electronics into an in-bra wearable unit that includes a user-attachable milk collection container. The following features do not, unless otherwise explicitly stated, require an external air pump, but should be expansively construed to cover breast pump systems that can utilise an external or internal air pump. Similarly, whilst the implementation described above is a breast pump system with a closed-loop air pump (i.e. the pump is protected from any possibility of milk contamination through the flexible membrane), the following features do not, unless otherwise explicitly stated, require a closed-loop air pump, but should be expansively construed to cover breast pump systems that are both closed loop and also open loop.

A. User Experience Innovations: Nipple Visibility

Feature 1: Visibility of the Nipple

One implementation of this invention envisages a wearable milk collection hub for a breast pump system that provides a clear and unobstructed view of the nipple for easy nipple alignment. This ensures that a correct alignment is maintained while pumping. The breast shield and outer shells are both substantially clear providing a clear and unobstructed view of the nipple when the assembled system is placed on the breast. This further enables the user to ensure proper nipple suction when the breast pump system is placed on the breast and while pumping.

We can generalize to:
A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the breast shield and the outer shell are substantially transparent, providing, to the mother placing the collection hub onto her breast, a clear and unobstructed view of the nipple to facilitate correct nipple alignment.

Feature 2: Visibility of the Nipple and of the Flexible Diaphragm

In addition to the clear and unobstructed view of the nipple, the system also provides a clear and unobstructed view of the diaphragm inside the hub. A user is able to see any movement of the diaphragm while pumping and ensure the system is correctly operating. The diaphragm is placed so as not to obstruct the line of sight to the nipple, hence providing both a view of the nipple and of the flexible diaphragm.

We can generalize to:
A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the breast shield and the outer shell are substantially transparent, providing simultaneously to the mother placing the collection hub onto her breast (i) a clear and unobstructed view of the nipple to facilitate correct nipple alignment and (ii) a view of the diaphragm to ensure the breast pump system is operating correctly.

Feature 3: Visibility of the Nipple and of a Substantial Part of Nipple Tunnel

The system is also able to provide an unobstructed view of the nipple tunnel for easy nipple alignment when the system is placed on the breast and while pumping. This further ensures that the spacing between the nipple and the side walls of the nipple tunnel is correctly positioned and maintained while pumping.

We can generalize to:
A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the breast shield and the outer shell are substantially transparent, providing to the mother placing the collection hub onto her breast (i) a clear and unobstructed view of the nipple to facilitate correct nipple alignment and (ii) a clear and unobstructed view of a substantial part of the nipple tunnel.

Feature 4: Diaphragm is Removably Mounted.

The wearable milk collection hub also includes a removable diaphragm that is configured to separate the air pump side from the milk side located in the hub, and thus prevents any contamination of the air pump unit by any milk. The diaphragm is shaped so that it includes portions which are either substantially parallel to the center axis of the nipple tunnel or substantially perpendicular to the center axis of the nipple tunnel.

We can generalize to:
A wearable milk collection hub for a breast pump system comprising:
(a) a substantially transparent breast shield made up of a breast flange and a nipple tunnel;
(b) a flexible diaphragm that is configured to prevent milk from reaching an external air pump subsystem;
(c) a substantially transparent outer shell that is configured to removably attach to the breast shield, such that the breast shield and outer shell form a vessel for collecting milk;
in which the diaphragm is removably mounted onto the breast shield and/or the outer shell, and in which the diaphragm includes a portion that is arranged over the end or tip of the nipple tunnel.

Feature 5: Specific Shape and Location of the Diaphragm

The diaphragm is also positioned so that it does not obstruct a mother's view of the nipple when placing the collection hub onto her breast. Hence a mother is able to see any movement of the diaphragm when the air pump is activated, thereby further ensuring the proper function of the breast pump system.

We can generalize to:

A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the diaphragm is removably mounted onto the breast shield and/or the outer shell and is positioned behind a diaphragm cap that forms part of the front or forward facing part of the outer shell, so as not to obstruct a mother's view of the nipple when placing the collection hub onto her breast.

B. Cost Engineering Innovations: Simplicity

Feature 6: Removable Diaphragm Cap

The wearable milk collection hub includes a removable diaphragm cap that is configured to cover and seal the diaphragm. The diaphragm cap is easily removable or attachable with a single push action when the collection hub has been placed onto the breast. The diaphragm cap includes an air port or hole to connect a tube between the milk collection hub and an external control unit housing a pump unit subsystem.

Hence a mother can place the collection hub on her breast first without the diaphragm cap and without the inconvenience of a tube connected to the air port. Once the milk collection hub is correctly placed on the breast, the mother can easily attach the diaphragm cap together with the tube with a single push action.

We can generalize to:

A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the outer shell includes a removable diaphragm cap that covers and seals the diaphragm; and in which the diaphragm cap forms part of the front or forward facing part of the outer shell and includes an air port configured to transfer negative air pressure from the external air pump subsystem to the diaphragm.

Feature 7: Removable Diaphragm Cap is Omnidirectional

A further advantage of the diaphragm cap is that it is omnidirectional and can be easily rotated on the rear surface of the outer shell, therefore providing the user with the ability to change or rotate the position of the air port on the diaphragm cap. This also helps the user modify the placement of a tube connected to the diaphragm cap. This feature also provides added versatility and/or flexibility to be used by different users and body shape with different clothing to achieve comfort and/or discretion.

We can generalize to:

A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
in which the outer shell includes a removable diaphragm cap that covers and seals the diaphragm; and in which the diaphragm cap forms part of the front or forward facing part of the outer shell and includes an air port configured to transfer negative air pressure from the external air pump subsystem to the diaphragm; and in which the removable diaphragm cap is configured to rotate to enable the position of the air port on the outer shell to be adjusted by a user.

Feature 8: 3 User-Removable Parts from the Breast Shield

We can generalize to:

A wearable milk collection hub for a breast pump system comprising:
(a) a breast shield made up of a breast flange and a nipple tunnel;
(b) a flexible diaphragm that is configured to prevent milk from reaching an external air pump subsystem;
(c) an outer shell that is configured to removably attach to the breast shield, such that the breast shield and outer shell form a vessel for collecting milk;
(d) a diaphragm cap that forms part of the front or forward facing part of the outer shell;
and in which the only user removable items from the breast shield are: the outer shell, the diaphragm, and the diaphragm cap, in normal use or normal disassembly.

C. User Experience Innovations: Low Noise

Feature 9: Airflow Block

We can generalize to:

A control unit for generating negative air pressure for a breast pump system, the control unit including:
(a) a rechargeable battery;
(b) a power charging circuit for controlling the charging of the rechargeable battery;
(c) control electronics powered by the rechargeable battery;
(d) a pump powered by the rechargeable battery and generating negative air pressure; and
(e) a motor for driving the pump;
(f) a casing;
in which the control unit further includes an airflow block that is configured to transfer suction from the pump to a suction or air port on the control unit and is further configured to attenuate sound from the pump and/or the motor reaching from reaching the casing.

Feature 10: Sound Valve

We can generalize to:

A control unit for generating negative air pressure for a breast pump system, the control unit including:
(a) a rechargeable battery;
(b) a power charging circuit for controlling the charging of the rechargeable battery;
(c) control electronics powered by the rechargeable battery;
(d) a pump powered by the rechargeable battery and generating negative air pressure; and
(e) a motor for driving the pump;
and in which the control unit further includes a sound valve that is configured to air to pass in and out of the control unit sufficient for pressure equalisation between the inside and outside of the control unit, while minimizing sound from the pump and/or motor escaping from the control unit.

Feature 11: Solenoid Foam Cap
We can generalize to:
A control unit for generating negative air pressure for a breast pump system, the control unit including:
(a) a rechargeable battery;
(b) a power charging circuit for controlling the charging of the rechargeable battery;
(c) control electronics powered by the rechargeable battery;
(d) a pump powered by the rechargeable battery and generating negative air pressure and;
(e) a motor for driving the pump;
(f) a solenoid valve for controlling the generated negative air pressure;
and in which the control unit further includes a cap or other structure that is configured to reduce the speed of air that enters the solenoid valve when the solenoid valve opens to ambient air pressure.

D. User Experience Innovations: Product Handling

Feature 12: Multifunction Mount
We can generalize to:
A control unit for generating negative air pressure for a breast pump system, the control unit including:
(a) a rechargeable battery;
(b) a power charging circuit for controlling the charging of the rechargeable battery;
(c) control electronics powered by the rechargeable battery;
(d) a pump powered by the rechargeable battery and generating negative air pressure and;
(e) a motor for driving the pump;
and in which the control unit further includes a removable multifunction mount configured to attach to the control unit in at least two different positions, such that the control unit can be held in either upright/portrait or longwise/landscape mode.

Feature 13: Tube Management Feature
We can generalize to:
A control unit for generating negative air pressure for a breast pump system, the control unit including:
(a) a rechargeable battery;
(b) a power charging circuit for controlling the charging of the rechargeable battery;
(c) control electronics powered by the rechargeable battery;
(d) a pump powered by the rechargeable battery and generating negative air pressure and;
(e) a motor for driving the pump;
and in which the control unit further includes or, is removably attached to a tube management structure configured to enable an air tube attachable to the control unit to be wound around that tube management structure.

Generally applicable optional features that can be combined with any one or more of the above features and can themselves be combined with one another:

Breast Shield
breast shield is rigid or semi-rigid.
breast shield is made up of a breast flange and a nipple tunnel; in which the nipple tunnel is configured to receive a nipple.
breast shield comes in different sizes, each of which are configured to attach to the same outer shell.
different sizes of the breast shield each provide a different spacing of the nipple from side walls of the nipple tunnel, when the breast shield is positioned onto a breast.
breast shield integrates the breast flange and nipple tunnel as a single one-piece item with no joins.
nipple tunnel includes a milk hole through which express milk flows into the milk collection hub via a non return valve.
breast shield includes a diaphragm housing that has sides that are parallel to the nipple tunnel.
diaphragm housing includes an air hole that transfers negative air pressure to the nipple tunnel.
air-pump chamber is a substantially annular chamber with walls that are parallel to the long or central axis of the nipple tunnel and those parallel walls lie over a region of the nipple tunnel that is subject in use to negative air pressure.
diaphragm housing has an outer, approximately cylindrical side wall that is generally parallel to the nipple tunnel, and an inner, approximately cylindrical side wall that is also is generally parallel to the nipple tunnel.
diaphragm housing has a front wall that forms the end of the nipple tunnel.
diaphragm housing has an annular rear wall that joins the outer and the inner sides walls and that annular rear wall lies over a region of the nipple tunnel that is subject in use to negative air pressure.
diaphragm moves within an air-pump chamber formed on one side by the diaphragm housing with walls that are parallel to the long or central axis of the nipple tunnel and on another side by the diaphragm cap.
breast shield is integrated with the diaphragm housing portion as a single, one piece moulded item.
breast shield includes a removable perimeter seal that provides an air-tight seal between an outer edge of the breast shield and the outer shell.
breast shield is a transparent or optically clear, dishwasher safe polypropylene, polycarbonate or copolyester, such as Tritan™, breast shield.

Outer Shell
outer shell is rigid.
the outer shell removably attaches, fits or latches onto the breast shield and so the breast shield provides a rear surface that is in contact with milk.
outer shell is attachable to the breast shield with a single push action.
outer shell attaches to the breast shield using magnets.
outer shell includes an air opening or vent hole such that atmospheric pressure is maintained inside the milk collection hub.
outer shell is directly removable from the breast shield in normal use or normal dis-assembly
outer shell is removable from the breast shield together with a flexible diaphragm that is attached, permanently or removably, to the outer shell.
outer shell is an integral part of the breast shield.
outer shell includes a diaphragm cap that sits over a diaphragm.
outer shell and diaphragm are together a single item.
outer shell includes a pouring opening which can be closed for transportation of the milk collection hub.
outer shell has a front surface that is curved to fit inside a bra and to contact the inner surface of the bra.
outer shell is a transparent or optically clear, dishwasher safe polypropylene, polycarbonate or copolyester, such as Tritan™, outer shell.
outer shell is a self-contained milk collection hub and so the breast shield does not provide a surface in contact with milk.

Diaphragm
- diaphragm is flexible, and deforms to create negative pressure.
- diaphragm is not sufficiently flexible to deform to create negative pressure but serves instead solely to prevent milk from passing through it and filling the air lines or reaching the motor.
- diaphragm is substantially rigid and serves instead solely to prevent milk from passing through it and filling the air lines or reaching the motor.
- diaphragm includes inner and outer side walls that are substantially parallel to the center axis of the nipple tunnel.
- diaphragm includes substantially cylindrical inner and outer side walls that are substantially parallel to the center axis of the nipple tunnel.
- diaphragm, when under negative pressure, moves past a milk opening in the nipple tunnel towards the over the end or tip of the nipple tunnel.
- diaphragm includes portions which are substantially parallel to the center axis of the nipple tunnel and includes portions which are substantially perpendicular to the center axis of the nipple tunnel.
- diaphragm is shaped to be flush to a diaphragm housing that has an outer, approximately cylindrical side wall that is generally parallel to the nipple tunnel, and an inner, approximately cylindrical concentric side wall that is also is generally parallel to the nipple tunnel.
- diaphragm flexes when negative air pressure is applied to it by an air pump subsystem, and transfers that negative air-pressure to pull the breast and/or nipple against the breast shield to cause milk to be expressed.
- diaphragm is positioned such as not to obstruct a mother's view of a substantial part of the nipple tunnel when placing the collection hub onto her breast;
- diaphragm is moulded as part of, or otherwise attached to, the outer shell.
- the outer shell and diaphragm are formed or joined together to form a single item.
- diaphragm includes portions that run substantially parallel to the center axis of the nipple tunnel.
- diaphragm is a single flexible membrane shaped to include inner and outer substantially cylindrical walls that are generally parallel to the center axis of the nipple tunnel.
- diaphragm includes a portion that sits over the end of the nipple tunnel, facing away from the breast.
- diaphragm is removably attached to the outer shell.
- diaphragm is removable from the outer shell for cleaning
- diaphragm is configured to self-seal under the negative air pressure to a
- diaphragm holder that is part of the breast shield.
- diaphragm is a one-piece item devoid of any holes or openings.
- diaphragm is permanently fixed to the outer shell.
- diaphragm is a single flexible membrane shaped to include inner and outer substantially cylindrical walls that are generally parallel to the center axis of the nipple tunnel, an annular wall that joins the inner and outer substantially cylindrical walls, and an end wall that sits over the end of the nipple tunnel.

Diaphragm Cap
- diaphragm cap is removable.
- diaphragm cap forms the front of the outer shell.
- diaphragm cap includes an air port that is configured to deliver air pressure to the milk collection hub.
- diaphragm cap is configured to fit or latch onto the outer shell with a single push action.
- diaphragm cap includes recesses or features configured to be gripped with the fingers of one hand.
- diaphragm cap includes a pair of recesses configured to enable the cap to be gripped and removed from the outer shell, and installed into the outer shell, with a single hand.
- diaphragm cap is rotatable in the outer shell to adjust the position of the air port on the diaphragm cap.
- diaphragm cap includes a passage way for the air tube.
- diaphragm cap includes a flat portion such that the milk collection hub can rest on a flat surface positioned on this flat portion.
- diaphragm cap is is shaped to fit inside an inner portion of a bra.
- diaphragm cap is a transparent or optically clear, dishwasher safe polypropylene, polycarbonate or copolyester, such as Tritan™, diaphragm cap.

Entire System
- the system is a closed system.
- the system has a capacity of approximately 5 fluid ounces (148 ml).
- width of the milk collection hub is of about 5.7 cm in the direction of the central axis of the nipple tunnel.
- each milk collection hub is, in-use, bra-worn, for example is shaped to be worn inside a maternity bra.
- the system makes less than 50 dB noise at maximum power when the motor is running, and preferably less than 45 dB.

Control Unit
- control unit is configured to control suction delivered to one or two wearable milk collection hubs.
- control unit houses an air pump subsystem that is configured to generate negative air pressure and transfer negative air pressure to a wearable milk collection hub.
- control unit does not house an air pump subsystem but controls an air pump that is external to the control unit
- air pump subsystem is held in place between a sound attenuating motor mount and an airflow block, each configured to absorb vibration from the pump unit.
- control unit includes a wireless data communications system powered by a rechargeable battery;
- control unit includes one or more buttons which are configured to control at least one wearable collection hub.
- control unit includes a visual and/or haptic indicator that indicates whether milk is flowing or not flowing into the hub.
- control unit includes a visual and/or haptic indicator that indicates the activated pumping profile or pattern.
- control unit includes a visual and/or haptic indicator that indicates the rechargeable battery status.
- control unit includes a USB charging socket connected to the power charging circuit;
- multifunction mount is an o-ring.

Airflow Block
- airflow block is configured transfer air or suction from the pump unit and also to absorb vibrations from the pump unit.
- airflow block is made of a compression moulded silicone.
- airflow block is directly connected to the air pump subsystem outlet.
- airflow block is located near a solenoid valve.
- airflow block is a one-piece item.
- control unit is sealed such as to further attenuate sound.

control unit includes an housing with a top portion and a bottom portion.

the bottom and top portions are sealed together using a seal perimeter.

airflow block is integrated with a portion of the seal perimeter.

airflow block connects to an air port or hole for a tube that delivers air to a wearable milk collection hub.

Sound Valve sound valve is configured to regulate the pressure inside the control unit so that the inside of the control unit remains at ambient pressure and also to attenuate noise from the pump unit escaping from inside the control unit.

sound valve is located on the bottom portion of the control unit.

sound valve includes a small cut that is configured to deform under pressure.

sound valve is made of silicone.

Foam Cap solenoid foam cap is configured to reduce the speed of air that enters the solenoid valve when the solenoid valve opens to ambient air pressure and hence to reduce the sound of that air entering the solenoid valve.

solenoid foam cap is a one piece item made of plastic.

foam cap includes one or more small opening or holes.

control unit also includes two silencers (or muffler) in which one silencer is connected to the solenoid valve and the other silencer is connected to the motor.

Note

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred example(s) of the invention, it will be apparent to those of ordinary skill in the art that numerous modifications can be made without departing from the principles and concepts of the invention as set forth herein.

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

What is claimed is:

1. A wearable milk collection hub comprising:
   a breast shield comprising:
      a breast flange;
      a nipple tunnel extending from the breast flange, the nipple tunnel comprising
      a closed end and a milk port, the milk port being intermediate to the breast flange and the closed end; and
      an outer edge;
   a diaphragm configured to deform to create negative air pressure in the nipple tunnel, at least a part of the diaphragm is arranged over the closed end of the nipple tunnel and concentric with the nipple tunnel; and
   an outer shell comprising an outer groove configured to receive the outer edge of the breast shield such that the outer shell is configured to be removably attachable to the breast shield, the outer shell further configured to receive expressed milk via the milk port.

2. The wearable milk collection hub of claim 1, wherein the outer shell is configured to be removably attachable to the breast shield such that the outer shell is configured to contact the breast shield at a rear end of the outer shell and the breast shield is configured to contact the expressed milk at a front end of the breast shield.

3. The wearable milk collection hub of claim 1, wherein the outer shell comprises a top end comprising a pouring opening configured to release the expressed milk.

4. The wearable milk collection hub of claim 1, wherein the outer shell comprises a base comprising a flat portion configured to allow the wearable milk collection hub to rest on a flat surface.

5. The wearable milk collection hub of claim 1, wherein the breast shield comprises a diaphragm housing part comprising an air hole configured to transfer negative air pressure to the nipple tunnel.

6. The wearable milk collection hub of claim 1, wherein the diaphragm is configured to be removably mounted between the breast shield and the outer shell.

7. The wearable milk collection hub of claim 1, wherein the breast shield and the outer shell are substantially transparent, providing to a user placing the wearable milk collection hub onto the user's breast a view of a nipple to facilitate correct nipple alignment, and
   wherein the outer shell is configured to support an air port configured to provide an air connection to a control unit via a tube.

8. A wearable milk collection hub configured to connect to an external negative pressure generating control unit comprising:
   a breast shield comprising:
      a breast flange;
      a nipple tunnel extending from the breast flange, the nipple tunnel comprising an end remote from the breast flange and a milk port intermediate to the breast flange and the end; and
      a diaphragm housing part;
   a diaphragm configured to:
      be removably mounted to the diaphragm housing part,
      extend over and adjacent to the milk port in a relaxed state, and
      deform based on negative air pressure generated by the control unit to create negative air pressure in the nipple tunnel; and
   an outer shell comprising a rear end configured to removably attach the outer shell to the breast shield such that the breast shield and the outer shell form a vessel to receive expressed milk via the milk port, a front end opposing the rear end, the front end comprising a curvature, a base intermediate to the rear end and the front end, and a top end opposing the base, the top end comprising a pouring opening configured to release the expressed milk.

9. The wearable milk collection hub of claim 8, wherein a structure comprising the diaphragm is configured to be at least partially arranged over the closed end of the nipple tunnel.

10. The wearable milk collection hub of claim 8, further comprising an air port configured to provide an air connection to the control unit via a tube.

11. The wearable milk collection hub of claim 10, further comprising a movable cap positioned over the air port.

12. The wearable milk collection hub of claim 11, wherein the movable cap is disposed on the front end of the outer shell.

13. The wearable milk collection hub of claim 8, wherein the breast shield and the outer shell are substantially transparent, providing to a user placing the wearable milk collection hub onto the user's breast a view of a nipple to facilitate correct nipple alignment, and
  wherein the wearable milk collection hub is shaped to be worn inside a bra.

14. The wearable milk collection hub of claim 8, wherein the rear end of the outer shell is configured to receive an outer edge of the breast shield such that an air-tight seal is formed between the breast shield and the outer shell.

15. The wearable milk collection hub of claim 8, wherein the breast shield is semi-rigid.

16. The wearable milk collection hub of claim 8, wherein the base comprises a flat portion configured to allow the wearable milk collection hub to rest on a flat surface.

17. A breast pump system comprising:
  a control unit comprising:
    a battery, and
    a pump configured to be powered by the battery and to generate negative air pressure; and
  a wearable milk collection hub configured to connect to the control unit via an air line, the wearable milk collection hub comprising:
    a breast shield comprising:
      a breast flange; and
      a nipple tunnel extending from the breast flange;
    a diaphragm configured to deform based on the negative air pressure generated by the pump to create negative air pressure in the nipple tunnel;
    an outer shell comprising a rear end configured to removably attach to the breast shield and, an interior volume between the outer shell and the breast shield defining a chamber to receive expressed milk; and
    a diaphragm cap configured to cover and seal the diaphragm at a front end of the outer shell, the front end being opposite to the rear end, the diaphragm cap forms a central region on a front surface of the outer shell.

18. The breast pump system of claim 17, wherein the breast shield comprises an outer edge configured to be received by the rear end of the outer shell.

19. The breast pump system of claim 17, wherein the interior volume is bounded by the rear end of the outer shell and a front end of the breast shield.

20. The breast pump system of claim 17, wherein the control unit further comprises:
  a wireless data communications system configured to be powered by the battery;
  one or more buttons configured to control the wearable milk collection hub;
  at least one of a visual indicator or a haptic indicator configured to indicate the activated pumping profile or pattern;
  at least one of a visual indicator or a haptic indicator configured to indicate a status of the battery; and
  a Universal Serial Bus (USB) charging socket configured to be connected to a power charging circuit.

21. The breast pump system of claim 17, further comprising a milk port through which the expressed milk flows into the chamber.

22. The breast pump system of claim 21, wherein the diaphragm is configured to extend over and adjacent to the milk port in a relaxed state.

23. The breast pump system of claim 21, further comprising a non-return valve configured to be mounted to the milk port.

24. The breast pump system of claim 17, wherein the diaphragm cap comprises an air port configured to receive an end of the air line.

25. The breast pump system of claim 24, wherein the diaphragm cap is configured such that the air port can be located above the nipple tunnel.

26. The breast pump system of claim 17, wherein the diaphragm cap comprises a pair of recessed finger grip features.

27. The breast pump system of claim 17, wherein at least a part of the diaphragm is arranged concentric with the nipple tunnel.

28. A breast pump system comprising:
  a control unit comprising:
    a battery, and
    a pump configured to be powered by the battery and to generate negative air pressure; and
  a wearable milk collection hub configured to connect to the control unit via an air line, the wearable milk collection hub comprising:
    a breast shield comprising:
      a breast flange; and
      a nipple tunnel extending from the breast flange;
    a diaphragm configured to deform based on the negative air pressure generated by the pump to create negative air pressure in the nipple tunnel, at least a part of the diaphragm is arranged concentric with the nipple tunnel;
    an outer shell comprising a rear end configured to removably attach to the breast shield, an interior volume between the outer shell and the breast shield defining a chamber to receive expressed milk; and
    a diaphragm cap configured to cover and seal the diaphragm at a front end of the outer shell, the front end being opposite to the rear end.

29. The breast pump system of claim 28, wherein the interior volume is bounded by the rear end of the outer shell and a front end of the breast shield.

30. The breast pump system of claim 28, wherein the diaphragm cap forms a central region on a front surface of the outer shell.

31. The breast pump system of claim 28, further comprising a milk port through which the expressed milk flows into the chamber, wherein the diaphragm is configured to extend over and adjacent to the milk port in a relaxed state.

32. The breast pump system of claim 28, wherein the diaphragm cap comprises an air port configured to receive an end of the air line.

33. The breast pump system of claim 28, wherein the diaphragm cap comprises a pair of recessed finger grip features.

* * * * *

UNITED STATES PATENT AND TRADEMARK OFFICE
CERTIFICATE OF CORRECTION

| | | |
|---|---|---|
| PATENT NO. | : 11,806,454 B2 | Page 1 of 1 |
| APPLICATION NO. | : 18/148864 | |
| DATED | : November 7, 2023 | |
| INVENTOR(S) | : De Becdelievre et al. | |

It is certified that error appears in the above-identified patent and that said Letters Patent is hereby corrected as shown below:

In the Claims

In Column 25, Claim 17, Line 32, delete "shield and," and insert -- shield, --, therefor.

Signed and Sealed this
Second Day of January, 2024

Katherine Kelly Vidal
*Director of the United States Patent and Trademark Office*